United States Patent
Shah

(10) Patent No.: US 10,543,037 B2
(45) Date of Patent: Jan. 28, 2020

(54) CONTROLLED NEUROMODULATION SYSTEMS AND METHODS OF USE

(71) Applicant: Medtronic Ardian Luxembourg S.a.r.l., Luxembourg (LU)

(72) Inventor: Jignesh M. Shah, San Jose, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 413 days.

(21) Appl. No.: 14/212,234

(22) Filed: Mar. 14, 2014

(65) Prior Publication Data

US 2014/0316402 A1 Oct. 23, 2014

Related U.S. Application Data

(60) Provisional application No. 61/801,091, filed on Mar. 15, 2013.

(51) Int. Cl.
*A61B 18/12* (2006.01)
*A61B 18/00* (2006.01)
(Continued)

(52) U.S. Cl.
CPC ...... *A61B 18/1206* (2013.01); *A61B 18/1492* (2013.01); *A61N 1/0551* (2013.01);
(Continued)

(58) Field of Classification Search
CPC .......... A61B 2018/00434; A61B 2018/00511; A61B 2018/00738; A61B 2018/00994;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

DE 10038737 2/2002
DE 102005041601 4/2007
(Continued)

OTHER PUBLICATIONS

Beale et al., "Minimally Invasive Treatment for Varicose Veins: A Review of Endovenous Laser Treatment and Radiofrequency Ablation". Lower Extremity Wounds 3(4), 2004, 10 pages.
(Continued)

*Primary Examiner* — Ronald Hupczey, Jr.
(74) *Attorney, Agent, or Firm* — Snell & Wilmer LLP

(57) ABSTRACT

The present disclosure relates to devices, systems and methods for positioning a neuromodulation device at a treatment site and evaluating the effects of therapeutic energy delivery applied to tissue in a patient. Before, during and/or after therapeutic energy delivery, a system can monitor parameters or values relevant to efficacious neuromodulation by emitting and detecting diagnostic energy at the treatment site. Feedback provided to an operator is based on the monitored values and relates to a relative position of the treatment device at the treatment site, as well as assessment of the likelihood that a completed treatment was technically successful.

20 Claims, 16 Drawing Sheets

(51) Int. Cl.
*A61N 1/36* (2006.01)
*A61N 1/05* (2006.01)
*A61B 18/14* (2006.01)
*A61B 8/12* (2006.01)
*A61B 90/00* (2016.01)
*A61B 8/00* (2006.01)

(52) U.S. Cl.
CPC ....... *A61N 1/3605* (2013.01); *A61N 1/36167* (2013.01); *A61B 8/12* (2013.01); *A61B 8/445* (2013.01); *A61B 2018/00011* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00904* (2013.01); *A61B 2090/061* (2016.02); *A61B 2090/3784* (2016.02)

(58) Field of Classification Search
CPC ......... A61B 7/00; A61B 7/0021; A61B 7/003; A61B 7/0052
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,770,653 A | 9/1988 | Shturman |
| 4,887,605 A | 12/1989 | Angelsen et al. |
| 4,890,623 A | 1/1990 | Cook et al. |
| 4,976,711 A | 12/1990 | Parins et al. |
| 5,109,859 A | 5/1992 | Jenkins |
| 5,284,153 A | 2/1994 | Raymond et al. |
| 5,295,484 A | 3/1994 | Marcus et al. |
| 5,300,068 A | 4/1994 | Rosar et al. |
| 5,301,683 A | 4/1994 | Durkan |
| 5,304,115 A | 4/1994 | Pflueger et al. |
| 5,358,514 A | 10/1994 | Schulman et al. |
| 5,365,172 A | 11/1994 | Hrovat et al. |
| 5,368,558 A | 11/1994 | Nita |
| 5,368,591 A | 11/1994 | Lennox et al. |
| 5,372,138 A | 12/1994 | Crowley et al. |
| 5,409,000 A | 4/1995 | Imran |
| 5,423,744 A | 6/1995 | Gencheff et al. |
| 5,425,364 A | 6/1995 | Imran |
| 5,484,400 A | 1/1996 | Edwards et al. |
| 5,531,520 A | 7/1996 | Grimson et al. |
| 5,571,147 A | 11/1996 | Sluijter et al. |
| 5,573,531 A | 11/1996 | Gregory |
| 5,588,964 A | 12/1996 | Imran et al. |
| 5,599,345 A | 2/1997 | Edwards et al. |
| 5,601,526 A | 2/1997 | Chapelon et al. |
| 5,626,576 A | 5/1997 | Janssen |
| 5,630,837 A | 5/1997 | Crowley |
| 5,672,174 A | 9/1997 | Gough et al. |
| RE35,656 E | 11/1997 | Feinberg |
| 5,688,266 A | 11/1997 | Edwards et al. |
| 5,700,282 A | 12/1997 | Zabara |
| 5,707,400 A | 1/1998 | Terry, Jr. et al. |
| 5,715,819 A | 2/1998 | Svenson et al. |
| 5,748,347 A | 5/1998 | Erickson |
| 5,772,590 A | 6/1998 | Webster, Jr. |
| 5,797,849 A | 8/1998 | Vesely et al. |
| 5,827,203 A | 10/1998 | Nita |
| 5,848,969 A | 12/1998 | Panescu et al. |
| 5,860,974 A | 1/1999 | Abele |
| 5,865,787 A | 2/1999 | Shapland et al. |
| 5,893,885 A | 4/1999 | Webster et al. |
| 5,904,651 A | 5/1999 | Swanson et al. |
| 5,944,710 A | 8/1999 | Dev et al. |
| 5,954,719 A | 9/1999 | Chen et al. |
| 5,957,941 A | 9/1999 | Ream |
| 5,967,984 A | 10/1999 | Chu et al. |
| 5,983,141 A | 11/1999 | Sluijter et al. |
| 6,004,269 A | 12/1999 | Crowley et al. |
| 6,009,877 A | 1/2000 | Edwards |
| 6,013,033 A | 1/2000 | Berger et al. |
| 6,024,740 A | 2/2000 | Lesh et al. |
| 6,033,357 A | 3/2000 | Ciezki et al. |
| 6,036,687 A | 3/2000 | Laufer et al. |
| 6,066,096 A | 5/2000 | Smith et al. |
| 6,066,134 A | 5/2000 | Eggers et al. |
| 6,079,414 A | 6/2000 | Roth |
| 6,083,159 A | 7/2000 | Driscoll, Jr. et al. |
| 6,091,995 A | 7/2000 | Ingle et al. |
| 6,099,524 A | 8/2000 | Lipson et al. |
| 6,117,101 A | 9/2000 | Diederich et al. |
| 6,120,516 A | 9/2000 | Selmon et al. |
| 6,121,775 A | 9/2000 | Pearlman |
| 6,135,999 A | 10/2000 | Fanton et al. |
| 6,142,991 A | 11/2000 | Schatzberger |
| 6,142,993 A | 11/2000 | Whayne et al. |
| 6,149,620 A | 11/2000 | Baker et al. |
| 6,161,048 A | 12/2000 | Sluijter et al. |
| 6,191,862 B1 | 2/2001 | Swanson et al. |
| 6,200,266 B1 | 3/2001 | Shokrollahi et al. |
| 6,219,577 B1 | 4/2001 | Brown, III et al. |
| 6,224,592 B1 | 5/2001 | Eggers et al. |
| 6,228,076 B1 | 5/2001 | Winston et al. |
| 6,238,389 B1 | 5/2001 | Paddock et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,296,619 B1 | 10/2001 | Brisken et al. |
| 6,309,379 B1 | 10/2001 | Willard et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,346,074 B1 | 2/2002 | Roth |
| 6,364,840 B1 | 4/2002 | Crowley |
| 6,389,311 B1 | 5/2002 | Whayne et al. |
| 6,394,956 B1 | 5/2002 | Chandrasekaran et al. |
| 6,398,780 B1 | 6/2002 | Farley et al. |
| 6,405,732 B1 | 6/2002 | Edwards et al. |
| 6,413,255 B1 | 7/2002 | Stern |
| 6,421,559 B1 | 7/2002 | Pearlman |
| 6,425,867 B1 | 7/2002 | Vaezy et al. |
| 6,445,939 B1 | 9/2002 | Swanson et al. |
| 6,447,505 B2 | 9/2002 | McGovern et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,517,534 B1 | 2/2003 | McGovern et al. |
| 6,522,913 B2 | 2/2003 | Swanson et al. |
| 6,522,926 B1 | 2/2003 | Kieval et al. |
| 6,527,765 B2 | 3/2003 | Kelman et al. |
| 6,542,781 B1 | 4/2003 | Koblish et al. |
| 6,546,272 B1 | 4/2003 | MacKinnon et al. |
| 6,549,800 B1 | 4/2003 | Atalar et al. |
| 6,552,796 B2 | 4/2003 | Magnin et al. |
| 6,562,034 B2 | 5/2003 | Edwards et al. |
| 6,570,659 B2 | 5/2003 | Schmitt |
| 6,572,551 B1 | 6/2003 | Smith et al. |
| 6,579,311 B1 | 6/2003 | Makower |
| 6,592,526 B1 | 7/2003 | Lenker |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,651,672 B2 | 11/2003 | Roth |
| 6,684,098 B2 | 1/2004 | Oshio et al. |
| 6,685,648 B2 | 2/2004 | Flaherty et al. |
| 6,711,429 B1 | 3/2004 | Gilboa et al. |
| 6,711,444 B2 | 3/2004 | Koblish |
| 6,716,184 B2 | 4/2004 | Vaezy et al. |
| 6,736,835 B2 | 5/2004 | Pellegrino et al. |
| 6,746,401 B2 | 6/2004 | Panescu |
| 6,752,805 B2 | 6/2004 | Maguire et al. |
| 6,763,261 B2 | 7/2004 | Casscells, III et al. |
| 6,770,070 B1 | 8/2004 | Balbierz |
| 6,797,960 B1 | 9/2004 | Spartiotis et al. |

(56) References Cited

U.S. PATENT DOCUMENTS

| | | |
|---|---|---|
| 6,802,857 B1 | 10/2004 | Walsh et al. |
| 6,823,205 B1 | 11/2004 | Jara |
| 6,845,267 B2 | 1/2005 | Harrison et al. |
| 6,849,075 B2 | 2/2005 | Bertolero et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,895,077 B2 | 5/2005 | Karellas et al. |
| 6,898,454 B2 | 5/2005 | Atalar et al. |
| 6,911,026 B1 | 6/2005 | Hall et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 6,955,175 B2 | 10/2005 | Stevens et al. |
| 6,986,739 B2 | 1/2006 | Warren et al. |
| 7,041,098 B2 | 5/2006 | Farley et al. |
| 7,087,051 B2 | 8/2006 | Bourne et al. |
| 7,100,614 B2 | 9/2006 | Stevens et al. |
| 7,112,196 B2 | 9/2006 | Brosch et al. |
| 7,149,574 B2 | 12/2006 | Yun et al. |
| 7,155,271 B2 | 12/2006 | Halperin et al. |
| 7,160,296 B2 | 1/2007 | Pearson et al. |
| 7,162,303 B2 | 1/2007 | Levin et al. |
| 7,197,354 B2 | 3/2007 | Sobe |
| 7,201,749 B2 | 4/2007 | Govari et al. |
| 7,221,979 B2 | 5/2007 | Zhou et al. |
| 7,238,184 B2 | 7/2007 | Megerman et al. |
| 7,247,141 B2 | 7/2007 | Makin et al. |
| 7,280,863 B2 | 10/2007 | Shachar |
| 7,310,150 B2 | 12/2007 | Guillermo et al. |
| 7,313,430 B2 | 12/2007 | Urquhart et al. |
| 7,343,195 B2 | 3/2008 | Strommer et al. |
| 7,381,200 B2 | 6/2008 | Katoh et al. |
| 7,390,894 B2 | 6/2008 | Weinshilboum et al. |
| 7,426,409 B2 | 9/2008 | Casscells, III et al. |
| 7,447,453 B2 | 11/2008 | Kim et al. |
| 7,473,224 B2 | 1/2009 | Makin |
| 7,473,890 B2 | 1/2009 | Grier et al. |
| 7,486,805 B2 | 2/2009 | Krattiger |
| 7,495,439 B2 | 2/2009 | Wiggins |
| 7,499,745 B2 | 3/2009 | Littrup et al. |
| 7,507,233 B2 | 3/2009 | Littrup et al. |
| 7,511,494 B2 | 3/2009 | Wedeen |
| 7,569,052 B2 | 8/2009 | Phan et al. |
| 7,591,996 B2 | 9/2009 | Hwang et al. |
| 7,599,730 B2 | 10/2009 | Hunter et al. |
| 7,603,166 B2 | 10/2009 | Casscells, III et al. |
| 7,617,005 B2 | 11/2009 | Demarais et al. |
| 7,620,451 B2 | 11/2009 | Demarais et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,662,114 B2 | 2/2010 | Seip et al. |
| 7,678,106 B2 | 3/2010 | Lee |
| 7,706,882 B2 | 4/2010 | Francischelli et al. |
| 7,717,853 B2 | 5/2010 | Nita |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,736,317 B2 | 6/2010 | Stephens et al. |
| 7,758,520 B2 | 7/2010 | Griffin et al. |
| 7,766,833 B2 | 8/2010 | Lee et al. |
| 7,766,878 B2 | 8/2010 | Tremaglio, Jr. et al. |
| 7,767,844 B2 | 8/2010 | Lee et al. |
| 7,769,427 B2 | 8/2010 | Shachar |
| 7,777,486 B2 | 8/2010 | Hargreaves et al. |
| 7,778,703 B2 | 8/2010 | Gross et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,806,871 B2 | 10/2010 | Li et al. |
| 7,811,265 B2 | 10/2010 | Hering et al. |
| 7,822,460 B2 | 10/2010 | Halperin et al. |
| 7,857,756 B2 | 12/2010 | Warren et al. |
| 7,863,897 B2 | 1/2011 | Slocum, Jr. et al. |
| 7,869,854 B2 | 1/2011 | Shachar et al. |
| 7,956,613 B2 | 6/2011 | Wald |
| 7,962,854 B2 | 6/2011 | Vance et al. |
| 7,983,751 B2 | 7/2011 | Zdeblick et al. |
| 8,031,927 B2 | 10/2011 | Karl et al. |
| 8,043,218 B2 | 10/2011 | Chapelon et al. |
| 8,052,604 B2 | 11/2011 | Lau et al. |
| 8,052,636 B2 | 11/2011 | Moll et al. |
| 8,131,371 B2 | 3/2012 | Demarais et al. |
| 8,131,372 B2 | 3/2012 | Levin et al. |
| 8,133,222 B2 | 3/2012 | Ormsby |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,757 B2 | 5/2012 | Jaffe et al. |
| 8,175,711 B2 | 5/2012 | Demarais et al. |
| 8,190,238 B2 | 5/2012 | Moll et al. |
| 8,192,053 B2 | 6/2012 | Owen et al. |
| 8,197,409 B2 | 6/2012 | Foley et al. |
| 8,198,611 B2 | 6/2012 | LaFontaine et al. |
| 8,221,407 B2 | 7/2012 | Phan et al. |
| 8,241,217 B2 | 8/2012 | Chiang et al. |
| 8,260,397 B2 | 9/2012 | Ruff et al. |
| 8,277,379 B2 | 10/2012 | Lau et al. |
| 8,295,912 B2 * | 10/2012 | Gertner .............. A61B 8/06 600/424 |
| 8,317,776 B2 | 11/2012 | Ferren et al. |
| 8,364,237 B2 | 1/2013 | Stone et al. |
| 8,403,881 B2 | 3/2013 | Ferren et al. |
| 8,409,172 B2 | 4/2013 | Moll et al. |
| 8,485,992 B2 | 7/2013 | Griffin et al. |
| 8,585,601 B2 * | 11/2013 | Sverdlik ............ A61B 17/2202 600/437 |
| 8,628,473 B2 * | 1/2014 | Sliwa ................ A61B 8/12 600/439 |
| 8,702,619 B2 | 4/2014 | Wang |
| 8,768,470 B2 | 7/2014 | Deem et al. |
| 8,909,316 B2 | 12/2014 | Ng |
| 8,977,359 B2 | 3/2015 | Rossing |
| 8,986,231 B2 * | 3/2015 | Gertner .............. A61B 5/412 600/437 |
| 9,002,446 B2 | 4/2015 | Wenzel et al. |
| 9,014,809 B2 | 4/2015 | Wenzel et al. |
| 9,014,821 B2 | 4/2015 | Wang |
| 9,022,948 B2 | 5/2015 | Wang |
| 9,314,300 B2 | 4/2016 | Nabutovsky et al. |
| 9,375,154 B2 | 6/2016 | Wang |
| 9,554,850 B2 | 1/2017 | Lee et al. |
| 9,579,030 B2 | 2/2017 | Scheuermann et al. |
| 2001/0007940 A1 | 7/2001 | Tu et al. |
| 2001/0051774 A1 | 12/2001 | Littrup et al. |
| 2002/0087208 A1 | 7/2002 | Koblish et al. |
| 2002/0095197 A1 | 7/2002 | Lardo et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0028114 A1 | 2/2003 | Casscells et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0069619 A1 | 4/2003 | Fenn et al. |
| 2003/0074039 A1 | 4/2003 | Puskas |
| 2003/0092995 A1 | 5/2003 | Thompson |
| 2003/0125790 A1 | 7/2003 | Fastovsky et al. |
| 2003/0181897 A1 | 9/2003 | Thomas et al. |
| 2003/0199747 A1 | 10/2003 | Michlitsch et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0111016 A1 | 6/2004 | Casscells et al. |
| 2004/0215186 A1 | 10/2004 | Cornelius et al. |
| 2004/0220556 A1 | 11/2004 | Cooper et al. |

(56) References Cited

U.S. PATENT DOCUMENTS

| | | |
|---|---|---|
| 2005/0080409 A1 | 4/2005 | Young et al. |
| 2005/0096647 A1 | 5/2005 | Steinke et al. |
| 2005/0148842 A1 | 7/2005 | Wang et al. |
| 2005/0154277 A1 | 7/2005 | Tang et al. |
| 2005/0187579 A1 | 8/2005 | Danek et al. |
| 2005/0203410 A1 | 9/2005 | Jenkins |
| 2005/0228286 A1 | 10/2005 | Messerly et al. |
| 2005/0228460 A1 | 10/2005 | Levin et al. |
| 2005/0256398 A1 | 11/2005 | Hastings et al. |
| 2006/0083194 A1 | 4/2006 | Dhrimaj et al. |
| 2006/0085054 A1 | 4/2006 | Zikorus et al. |
| 2006/0095029 A1 | 5/2006 | Young et al. |
| 2006/0095096 A1 | 5/2006 | DeBenedictis et al. |
| 2006/0100618 A1 | 5/2006 | Chan et al. |
| 2006/0122508 A1 | 6/2006 | Slayton et al. |
| 2006/0149166 A1 | 7/2006 | Zvuloni |
| 2006/0167106 A1 | 7/2006 | Zhang et al. |
| 2006/0171895 A1 | 8/2006 | Bucay-Couto |
| 2006/0206150 A1 | 9/2006 | Demarais et al. |
| 2006/0239921 A1 | 10/2006 | Mangat et al. |
| 2006/0271111 A1 | 11/2006 | Demarais et al. |
| 2007/0027390 A1 | 2/2007 | Maschke et al. |
| 2007/0049924 A1 | 3/2007 | Rahn |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0129720 A1 | 6/2007 | Demarais et al. |
| 2007/0197891 A1 | 8/2007 | Shachar et al. |
| 2007/0208256 A1 | 9/2007 | Marilla |
| 2007/0208301 A1 | 9/2007 | Evard et al. |
| 2007/0239062 A1 | 10/2007 | Chopra et al. |
| 2007/0265687 A1 | 11/2007 | Deem et al. |
| 2007/0278103 A1 | 12/2007 | Hoerr et al. |
| 2008/0039746 A1 | 2/2008 | Hissong et al. |
| 2008/0039830 A1 | 2/2008 | Munger et al. |
| 2008/0071269 A1 | 3/2008 | Hilario et al. |
| 2008/0082109 A1 | 4/2008 | Moll et al. |
| 2008/0091104 A1 | 4/2008 | Abraham |
| 2008/0091193 A1 | 4/2008 | Kauphusman et al. |
| 2008/0108867 A1 | 5/2008 | Zhou |
| 2008/0125772 A1* | 5/2008 | Stone ............... A61B 18/1492 606/41 |
| 2008/0161662 A1 | 7/2008 | Golijanin et al. |
| 2008/0221448 A1 | 9/2008 | Khuri-Yakub et al. |
| 2008/0294037 A1 | 11/2008 | Richter |
| 2008/0312673 A1 | 12/2008 | Viswanathan et al. |
| 2008/0319513 A1 | 12/2008 | Pu et al. |
| 2009/0030312 A1 | 1/2009 | Hadjicostis |
| 2009/0036948 A1 | 2/2009 | Levin et al. |
| 2009/0069671 A1 | 3/2009 | Anderson |
| 2009/0118620 A1 | 5/2009 | Tgavalekos et al. |
| 2009/0125099 A1 | 5/2009 | Weber et al. |
| 2009/0131789 A1 | 5/2009 | Fehre et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0240249 A1 | 9/2009 | Chan et al. |
| 2009/0270850 A1 | 10/2009 | Zhou et al. |
| 2010/0030061 A1 | 2/2010 | Canfield et al. |
| 2010/0087782 A1 | 4/2010 | Ghaffari et al. |
| 2010/0106005 A1 | 4/2010 | Karczmar et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0168624 A1 | 7/2010 | Sliwa |
| 2010/0191112 A1 | 7/2010 | Demarais et al. |
| 2010/0217162 A1 | 8/2010 | Hissong et al. |
| 2010/0222851 A1 | 9/2010 | Deem et al. |
| 2010/0222854 A1 | 9/2010 | Demarais et al. |
| 2010/0249604 A1 | 9/2010 | Hastings et al. |
| 2011/0009750 A1 | 1/2011 | Taylor et al. |
| 2011/0021976 A1 | 1/2011 | Li et al. |
| 2011/0071400 A1 | 3/2011 | Hastings et al. |
| 2011/0071401 A1 | 3/2011 | Hastings et al. |
| 2011/0087100 A1 | 4/2011 | Grossman |
| 2011/0112400 A1 | 5/2011 | Emery et al. |
| 2011/0144479 A1 | 6/2011 | Hastings et al. |
| 2011/0146673 A1 | 6/2011 | Keast et al. |
| 2011/0178403 A1 | 7/2011 | Weng et al. |
| 2011/0257523 A1 | 10/2011 | Hastings et al. |
| 2011/0257641 A1 | 10/2011 | Hastings et al. |
| 2011/0257642 A1 | 10/2011 | Griggs, III |
| 2011/0270120 A1 | 11/2011 | McFarlin et al. |
| 2011/0306851 A1 | 12/2011 | Wang |
| 2012/0029504 A1 | 2/2012 | Afonso et al. |
| 2012/0059241 A1 | 3/2012 | Hastings et al. |
| 2012/0065506 A1 | 3/2012 | Smith |
| 2012/0095335 A1 | 4/2012 | Sverdlik et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172837 A1 | 7/2012 | Demarais et al. |
| 2012/0172870 A1 | 7/2012 | Jenson et al. |
| 2012/0184850 A1 | 7/2012 | Gutierrez et al. |
| 2012/0191079 A1 | 7/2012 | Moll et al. |
| 2012/0209261 A1* | 8/2012 | Mayse ............... A61B 8/12 606/41 |
| 2012/0296232 A1 | 11/2012 | Ng |
| 2012/0296329 A1 | 11/2012 | Ng |
| 2013/0023865 A1 | 1/2013 | Steinke et al. |
| 2013/0066316 A1 | 3/2013 | Steinke et al. |
| 2013/0085489 A1 | 4/2013 | Fain et al. |
| 2013/0123778 A1 | 5/2013 | Richardson et al. |
| 2013/0165764 A1 | 6/2013 | Scheuermann et al. |
| 2013/0172878 A1 | 7/2013 | Smith |
| 2013/0218029 A1 | 8/2013 | Cholette et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0025069 A1* | 1/2014 | Willard ............... A61B 18/1492 606/41 |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0135715 A1 | 5/2014 | Lambert et al. |
| 2014/0163360 A1 | 6/2014 | Stevens-Wright et al. |
| 2014/0163372 A1 | 6/2014 | Deladi et al. |
| 2014/0165764 A1 | 6/2014 | Moon et al. |
| 2014/0180077 A1 | 6/2014 | Huennekens et al. |
| 2014/0180197 A1 | 6/2014 | Sverdlik et al. |
| 2014/0180273 A1* | 6/2014 | Nair ............... A61B 18/1492 606/34 |
| 2014/0188103 A1 | 7/2014 | Millett |
| 2014/0194866 A1 | 7/2014 | Wang |
| 2014/0213873 A1 | 7/2014 | Wang |
| 2014/0221805 A1 | 8/2014 | Wang |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0112329 A1 | 4/2015 | Ng |

(56) References Cited

U.S. PATENT DOCUMENTS

| | | |
|---|---|---|
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |
| 2015/0289770 A1 | 10/2015 | Wang |
| 2015/0289929 A1 | 10/2015 | Toth et al. |
| 2015/0366609 A1 | 12/2015 | Richardson et al. |
| 2016/0000345 A1 | 1/2016 | Kobayashi et al. |
| 2016/0029960 A1 | 2/2016 | Toth et al. |
| 2016/0038028 A1 | 2/2016 | Buelna et al. |
| 2016/0081744 A1 | 3/2016 | Wang |
| 2016/0324572 A1 | 11/2016 | Gross et al. |
| 2016/0331451 A1 | 11/2016 | Nabutovsky et al. |
| 2016/0331453 A1 | 11/2016 | Fain et al. |
| 2016/0374568 A1 | 12/2016 | Wang et al. |

FOREIGN PATENT DOCUMENTS

| | | |
|---|---|---|
| EP | 1169976 | 1/2002 |
| EP | 1181895 A2 | 2/2002 |
| EP | 1579889 A1 | 9/2005 |
| EP | 1634542 A1 | 3/2006 |
| EP | 1906853 A2 | 4/2008 |
| EP | 2197533 A1 | 6/2010 |
| EP | 2316371 | 5/2011 |
| EP | 2320821 A1 | 5/2011 |
| EP | 2378956 A2 | 10/2011 |
| EP | 2460486 | 6/2012 |
| EP | 2594193 | 5/2013 |
| EP | 2613704 | 7/2013 |
| EP | 2747691 | 7/2014 |
| EP | 2797535 A1 | 11/2014 |
| EP | 2852339 | 4/2015 |
| EP | 2866645 | 5/2015 |
| EP | 2887900 | 7/2015 |
| EP | 2907464 | 8/2015 |
| EP | 2914334 | 9/2015 |
| EP | 2967383 | 1/2016 |
| EP | 2978372 | 2/2016 |
| EP | 3178428 | 6/2017 |
| EP | 3178432 | 6/2017 |
| JP | H08504531 | 5/1996 |
| JP | H1071037 | 3/1998 |
| JP | 2001518808 | 10/2001 |
| JP | 2005278739 | 10/2005 |
| JP | 2008515544 | 5/2008 |
| JP | 2009539565 | 11/2009 |
| JP | 2010162163 | 7/2010 |
| JP | 2010533513 | 10/2010 |
| JP | 2011505929 | 3/2011 |
| WO | WO-2014091328 | 7/1989 |
| WO | WO-199407446 A1 | 4/1994 |
| WO | WO-9501751 A1 | 1/1995 |
| WO | WO-1995025472 | 9/1995 |
| WO | WO-9531142 A1 | 11/1995 |
| WO | WO-1997036548 | 10/1997 |
| WO | WO 1998042403 | 10/1998 |
| WO | WO-9858588 A1 | 12/1998 |
| WO | WO-1999/00060 | 1/1999 |
| WO | WO-9900060 A1 | 1/1999 |
| WO | WO-9916370 A1 | 4/1999 |
| WO | WO-0059394 A1 | 10/2000 |
| WO | WO-2001022897 | 4/2001 |
| WO | WO-2001070114 | 9/2001 |
| WO | WO-02089686 A1 | 11/2002 |
| WO | WO-2003022167 | 3/2003 |
| WO | WO-03026525 A1 | 4/2003 |
| WO | WO-2003082080 | 10/2003 |
| WO | WO-2004110258 A2 | 12/2004 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO 2006105121 | 10/2006 |
| WO | WO-2006/116256 | 11/2006 |
| WO | WO-2006116198 A2 | 11/2006 |
| WO | WO-2007008954 | 1/2007 |
| WO | WO-2007078997 A2 | 7/2007 |
| WO | WO-2008003058 | 1/2008 |
| WO | WO-2008049084 A2 | 4/2008 |
| WO | WO-2008102363 A2 | 8/2008 |
| WO | WO-2009036471 A1 | 3/2009 |
| WO | WO-2009137819 A1 | 11/2009 |
| WO | WO-2010/009452 | 1/2010 |
| WO | WO-2010/011763 | 1/2010 |
| WO | WO-2010042653 A1 | 4/2010 |
| WO | WO-2010078175 | 7/2010 |
| WO | WO-2010102310 A2 | 9/2010 |
| WO | WO-2011089935 | 7/2011 |
| WO | WO-2012033974 | 3/2012 |
| WO | WO-2012068471 | 5/2012 |
| WO | WO-2012/103108 | 8/2012 |
| WO | WO-2012158864 | 11/2012 |
| WO | WO-2013009977 | 1/2013 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014089380 | 6/2014 |
| WO | WO-2014091401 | 6/2014 |
| WO | WO-2014100226 | 6/2014 |
| WO | WO-2014/149552 A1 | 9/2014 |
| WO | WO-2014/149553 A1 | 9/2014 |
| WO | WO-2014/149690 A2 | 9/2014 |
| WO | WO-2014149550 A2 | 9/2014 |
| WO | WO-2014150425 A1 | 9/2014 |
| WO | WO-2014150432 A1 | 9/2014 |
| WO | WO-2014150441 A2 | 9/2014 |
| WO | WO-2014150455 A1 | 9/2014 |
| WO | WO-2014/158713 A1 | 10/2014 |
| WO | WO-2014158708 A1 | 10/2014 |
| WO | WO-2014163990 A1 | 10/2014 |
| WO | WO-2014/179768 A1 | 11/2014 |
| WO | WO-2014/182946 A2 | 11/2014 |

OTHER PUBLICATIONS

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

European Search Report for European Application No. 13159256, dated Oct. 17, 2013, 6 pages.

International Search Report and Written Opinion for International Application No. PCT/US2014/029860, dated May 26, 2014, 13 pages.

Chinushi et al., "Blood Pressure and Autonomic Responses to Electrical Stimulation of the Renal Arterial Nerves Before and After Ablation of the Renal Artery." Hypertension, 2013, 61, pp. 450-456.

(56) References Cited

OTHER PUBLICATIONS

Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 am, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).

(56) References Cited

OTHER PUBLICATIONS

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal deneravation on haemodynamic and excretory functions on the ipsilateral and contralateral kidney in the cat." Hypertension, 4:181-188 (1986).

Stouffer, G. A. et al., Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium rentention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter,"Journal of the American College of Cardiology, 1999; 33; pp. 972-984.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, Time, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

(56) References Cited

OTHER PUBLICATIONS

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009.

Schlaich, M.P. et al., "Renal Denervation as a Therapeutic Approach for Hypertension: Novel Implictions for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16:160.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

International Search Report and Written Opinion for International Application No. PCT/US2014/029860, dated May 26, 2014 12 pages.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.

Opposition to European U.S. Pat. No. 2,465,470, Granted Oct. 28, 2015, Date of Opposition Jul. 27, 2016, 34 pp.

U.S. Appl. No. 11/363,867, filed Feb. 27, 2006, 70 pp.

U.S. Appl. No. 60/813,589, filed Dec. 29, 2005, 62 pp.

Ureter, https://en.wikipedia.org/wiki/Ureter, Jun. 2016, 6 pp.

Pieper et al., "Design and Implementation of a New Computerized System for Intraoperative Cardiac Mapping." Journal of Applied Physiology, 1991, vol. 71, No. 4, pp. 1529-1539.

Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.

U.S. Appl. No. 60/852,787, filed Oct. 18, 2006, 112 pages.

* cited by examiner

Arterial Vasculature

Venous Vasculature

CONTROLLED NEUROMODULATION SYSTEMS AND METHODS OF USE

CROSS-REFERENCE TO RELATED APPLICATION(S)

This application claims the benefit of U.S. Provisional Patent Application No. 61/801,091, filed Mar. 15, 2013, the disclosure of which is incorporated herein by reference in its entirety.

TECHNICAL FIELD

The present technology relates generally to monitoring neuromodulation and associated systems and methods. In particular, several embodiments are directed to endovascular monitoring systems and associated systems and methods.

BACKGROUND

The sympathetic nervous system (SNS) is a primarily involuntary bodily control system typically associated with stress responses. SNS fibers that innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate that result from renal sympathetic efferent stimulation are likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

Figure 1:
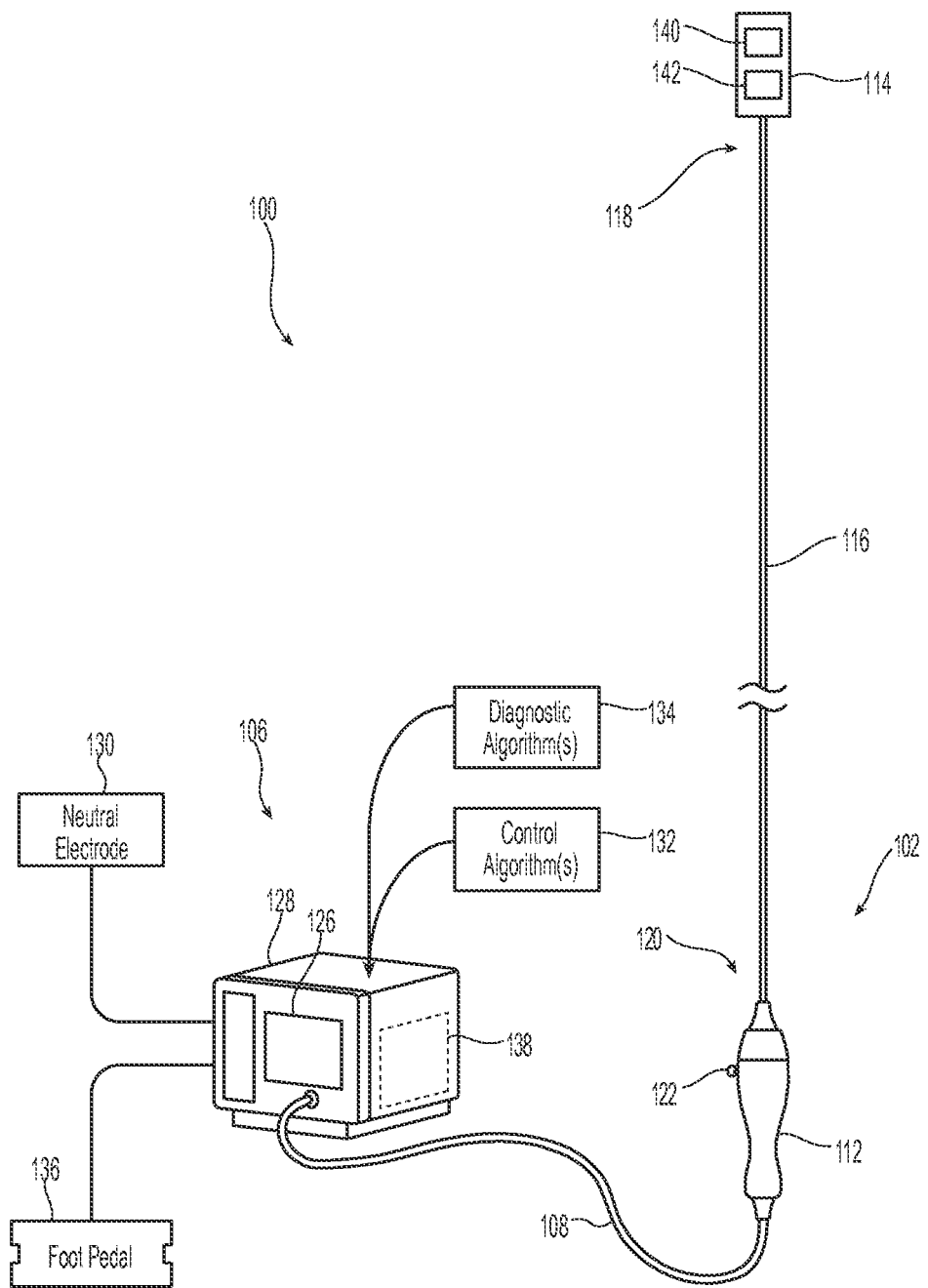
FIG. 1 is a partially-schematic perspective view illustrating a renal neuromodulation system including a treatment device configured in accordance with an embodiment of the present technology.

Specific details of several embodiments of the present technology are described herein with reference to FIGS. 1-13B. Although many of the embodiments are described herein with respect to devices, systems, and methods for modulation of renal nerves using electrode-based, transducer-based, element-based, cryotherapeutic, and chemical-based approaches, other applications and other treatment modalities in addition to those described herein are within the scope of the present technology. Additionally, other embodiments of the present technology can have different configurations, components, or procedures than those described herein. For example, other embodiments can include additional elements and features beyond those described herein, or other embodiments may not include several of the elements and features shown and described herein. For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function. Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device.

I. Renal Neuromodulation

Renal neuromodulation is the partial or complete incapacitation or other effective disruption of nerves innervating the kidneys (e.g., rendering neural fibers inert or inactive or otherwise completely or partially reduced in function). For example, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics.

Thermal heating effects described herein can include both thermal ablation and non-ablative thermal alteration or damage (e.g., via sustained heating and/or resistive heating). Desired thermal heating effects may include raising the temperature of target neural fibers above a desired threshold temperature to achieve non-ablative thermal alteration, or above a higher threshold temperature to achieve ablative thermal alteration.

Various techniques can be used to partially or completely incapacitate neural pathways, such as those innervating the kidneys. The purposeful application of energy (e.g., radiofrequency energy, mechanical energy, acoustic energy, electrical energy, thermal energy, light, etc.) to tissue and/or the purposeful removal of energy (e.g., thermal energy) from tissue can induce one or more desired thermal heating and/or cooling effects on localized regions of the tissue. The tissue, for example, can be tissue of the renal artery and adjacent regions of the renal plexus (RP), which lay intimately within or adjacent to the adventitia of the renal artery. For example, the purposeful application and/or removal of energy can be used to achieve therapeutically effective neuromodulation along all or a portion of the renal plexus (RP).

In the era of evidence-based medicine, evaluating the efficacy of an ablation treatment, such as neuromodulation, can be important in gauging whether a treated patient may need additional neuromodulation treatment and/or alternative treatment. Neuromodulation efficacy is currently assessed by measuring and analyzing various physiological parameters (e.g., heart rate, blood pressure, etc.). However, statistically meaningful changes in such physiological parameters may not be observed until at least two weeks (and in most cases, months) after completion of the treatment. In the absence of real-time or at least relatively contemporaneous feedback, nerves that are under ablated, over ablated, or missed altogether may go undetected, rendering the treatment unsuccessful. As a result, an unsuccessful treatment may not be clinically addressed until weeks or months after the initial treatment. Even then, the treatment will be categorized as "successful" or "not successful" but the cause of the non-success will remain unknown. To address this need, the present technology provides several embodiments of devices, systems, and methods that facilitate relatively rapid analysis of neuromodulation efficacy by using return energy of diagnostic ultrasound and/or electromagnetic energy, such as optical energy, emissions to characterize neuromodulated nerve and tissue as well as provide positional feedback to facilitate positioning of the device.

II. Systems and Methods for Neuromodulation

FIG. 1 is a partially-schematic diagram illustrating a system 100 configured in accordance with an embodiment of the present technology. The system 100 can include a treatment device 102 (e.g., a catheter) operably coupled to a console 106 via a connector 108 (e.g., a cable). As shown in FIG. 1, the treatment device 102 can include an elongated shaft 116 having a proximal portion 120, a handle assembly 112 at a proximal region of the proximal portion 120, and a distal portion 118 extending distally relative to the proximal portion 120. The elongated shaft 116 can be configured to locate the distal portion 118 intravascularly (e.g., within a renal artery) or within another suitable body lumen (e.g., within a ureter) at a treatment location. The treatment device 102 can further include a treatment assembly 114 carried by or affixed to the distal portion 118 of the elongated shaft 116. The treatment assembly 114 can include a neuromodulation element 140 (shown schematically in FIG. 1) configured to deliver a therapeutic energy or compound to a nerve located at least proximate to a wall of a body lumen and one or more transducers 142 (also shown schematically in FIG. 1) configured to emit diagnostic energy toward the tissue as well as detect a return energy of the emitted diagnostic energy.

The console 106 can be configured to control, monitor, supply, or otherwise support operation of the treatment device 102. For example, the console 106 can include an energy generator configured to generate a selected form and magnitude of therapeutic, neuromodulation energy (e.g., radiofrequency energy ("RF"), pulsed energy, microwave energy, optical energy, ultrasound energy (e.g., high intensity focused ultrasound energy or non-focused ultrasound energy), direct heat energy or another suitable type of energy) for delivery to the target treatment site via the neuromodulation element 140. In some embodiments, neuromodulation may be achieved by a chemical treatment including delivering one or more chemicals (e.g., guanethidine, ethanol, phenol, a neurotoxin (e.g., vincristine)), or another suitable agent selected to alter, damage, or disrupt nerves. In some embodiments, the console 106 can store cooling fluid that can be transferred to the treatment device 102 (via the connector 108) for cryotherapeutic neuromodulation.

The console 106 can further be configured to generate a selected form and magnitude of diagnostic energy and/or a signal that causes the transducer 142 to produce diagnostic energy for emission and reflection and/or absorption at a treatment site. Suitable diagnostic energies include diagnostic ultrasound (e.g., acoustic) and electromagnetic radiation (e.g., optical energy). Diagnostic energy provided for emission/detection purposes differs from therapeutic ultrasound and/or electromagnetic energy used to cause neuromodulation. In some embodiments, the console 106 can be configured to generate and transmit (via the connector 108) the neuromodulation energy and a signal that causes the transducer 142 to produce diagnostic energy to the treatment assembly 114. For example, the system 100 can include a synchronization algorithm (FIG. 4B) that facilitates simultaneous and/or coordinated delivery of at least two different energy modalities to the treatment device 102 (e.g., RF and diagnostic ultrasound, therapeutic ultrasound and diagnostic ultrasound, etc.). In other embodiments, the system 100 can include a neuromodulation console (not shown) and a separate diagnostic console (not shown). The neuromodulation console can be operably connected to the neuromodulation element 140 and configured to generate neuromodulation energy. The diagnostic console (not shown) can be operably connected to the transducer 142 and configured to generate diagnostic energy.

The console 106 can be electrically coupled to the treatment device 102 via the connector 108 (e.g., a cable). One or more supply wires (not shown) can pass along the elongated shaft 116 or through a lumen in the elongated shaft 116 to the neuromodulation element 140 and/or the transducer 142 to transmit the required energy to the neuromodulation element 140 and/or the signals to the transducer 142. A control mechanism, such as foot pedal 136, may be connected (e.g., pneumatically connected or electrically connected) to the console 106 to allow the operator to initiate, terminate and, optionally, adjust various operational characteristics of the console 106, including, but not limited to, power delivery.

The console 106 can also be configured to deliver the neuromodulation energy via an automated control algorithm 132 and/or under the control of a clinician. In addition, one or more diagnostic algorithms 134 may be executed on a processor (not shown) of the system 100. Such diagnostic algorithms 134 can provide feedback to the clinician, such as via an indicator 126 (e.g., a display, a user interface, one or more LEDs, etc.) associated with the console 106 and/or system 100. For example, the console 106 may include an optional user interface that can receive user input and/or provide information to the user and/or processing circuitry for monitoring one or more optional sensors (e.g., pressure, temperature, impedance, flow, chemical, ultrasound, electromagnetic, etc.) of the treatment assembly 114 and/or treatment device 102. The feedback from the diagnostic information may allow a clinician to better position the device at the treatment site and/or determine the effectiveness of the applied energy during the treatment and/or shortly thereafter (e.g., while the patient is still catheterized). Likewise, while the patient is still catheterized, a clinician may decide to repeat a treatment based on feedback from the diagnostic information. Accordingly, this feedback may be useful in helping the clinician increase the likelihood of success of the current or subsequent treatments. Further details regarding suitable control algorithms 132 and diagnostic algorithms 134 are described below with reference to FIGS. 4A-10.

The system 100 can further include a controller 138 having, for example, memory (not shown), storage devices (e.g., disk drives), one or more output devices (e.g., a display), one or more input devices (e.g., a keyboard, a touchscreen, etc.) and processing circuitry (not shown). The output devices may be configured to communicate with the treatment device 102 (e.g., via the connector 108) to control power to the neuromodulation element 140 and/or transducer 142. In some embodiments the output devices can further be configured to obtain signals from the neuromodulation element 140, the transducer 142, and/or any associated sensors. Display devices may be configured to provide indications of power levels or sensor data, such as audio, visual or other indications, and/or the display devices may be configured to communicate the information to another device.

In some embodiments, the controller 138 can be part of the console 106, as shown in FIG. 1. Additionally or alternatively, the controller 138 can be personal computer(s), server computer(s), handheld or laptop device(s), multiprocessor system(s), microprocessor-based system(s), programmable consumer electronic(s), digital camera(s), network PC(s), minicomputer(s), mainframe computer(s), tablets, and/or any suitable computing environment. The memory and storage devices are computer-readable storage media that may be encoded with non-transitory, computer-executable instructions (e.g., the control algorithm(s), the feedback algorithm(s), etc.). In addition, the instructions, data structures, and message structures may be stored or transmitted via a data transmission medium, such as a signal on a communications link and may be encrypted. Various communications links may be used, such as the Internet, a local area network, a wide area network, a point-to-point dial-up connection, a cell phone network, Bluetooth, RFID, and other suitable communication channels. The system 100 may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

The neuromodulation element 140 of the treatment assembly 114 can be configured to modulate one or more renal nerves within tissue at or at least proximate to a wall of the renal vessel or lumen. The neuromodulation element 140 can include one or more energy delivery elements (e.g., electrodes) (not shown). For example, in some embodiments, the neuromodulation element 140 can be a single energy delivery element located at a distal portion 118 of the treatment assembly 114. In other embodiments, the neuromodulation element 140 can include two or more energy delivery elements. The energy delivery elements can be separate band electrodes spaced apart from each other along a portion of the length of the shaft 116. The electrodes can be adhesively bonded to a support structure at different positions along the length of the shaft 116. In some embodiments, the energy delivery elements can be formed from a suitable electrically conductive material (e.g., a metal, such as gold, platinum, alloys of platinum and iridium, etc.). The number, arrangement, shape (e.g., spiral and/or coil electrodes) and/or composition of the energy delivery elements may vary. The individual energy delivery elements of the neuromodulation element 140 can be electrically connected to the handle assembly 112 and/or the console 106 by a conductor or bifilar wire extending through a lumen of the shaft 116.

Figure 3:
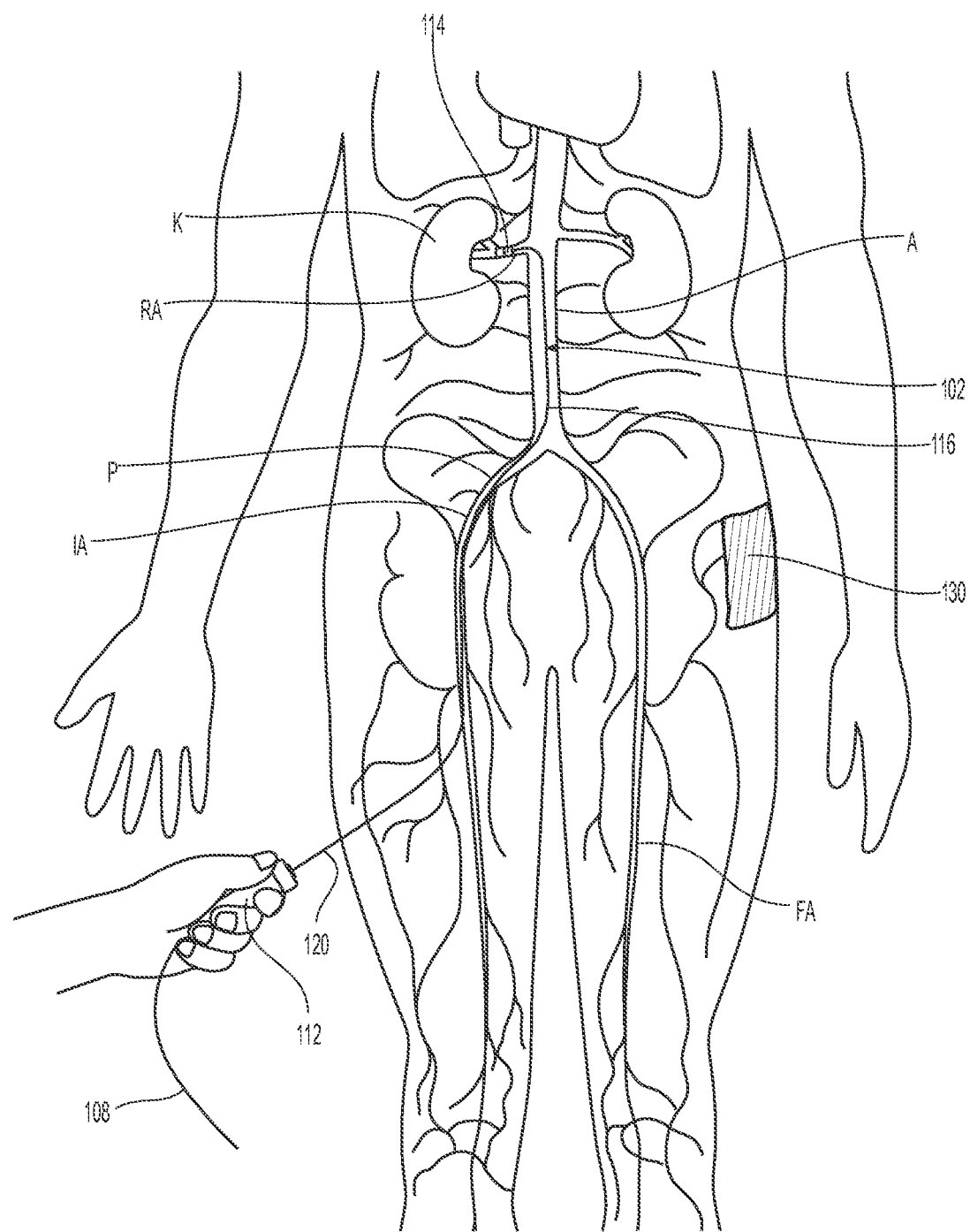
FIG. 3 is a partially cross-sectional anatomical front view illustrating advancing the treatment device shown in FIG. 1 along an intravascular path in accordance with an embodiment of the present technology.

In embodiments where the neuromodulation element 140 includes multiple energy delivery elements, the energy delivery elements may deliver power independently (e.g., may be used in a monopolar fashion), either simultaneously, selectively, or sequentially, and/or may deliver power between any desired combination of the elements (e.g., may be used in a bipolar fashion). Furthermore, the clinician optionally may be permitted to choose which energy delivery element(s) are used for power delivery in order to form highly customized lesion(s) within the vessel (e.g., the renal artery) or other body lumens (e.g., the ureter), as desired. In some embodiments, the system 100 may be configured to provide delivery of a monopolar electric field via the neuromodulation element 140. In such embodiments, a neutral or dispersive electrode 130 may be electrically connected to the console 106 and attached to the exterior of the patient (as shown in FIG. 3).

The transducer 142 can include an emitter 144 (FIG. 2A) configured to emit energy (e.g. ultrasound or electromagnetic energy) and/or a detector 146 (FIGS. 2B and 2C) configured to detect a return energy of the emitted energy. In some embodiments, the transducer 142 can comprise an emitter 144 or a detector 146, but not both. In these and other embodiments, the treatment assembly 114 can include two or more transducers 142 (e.g., one to emit and one to detect). Likewise, in many of the embodiments described herein, the transducer 142 (e.g., ultrasound and/or optical) can be configured to produce an energy emission and detect return energy of its own energy emissions.

Figure 2A:
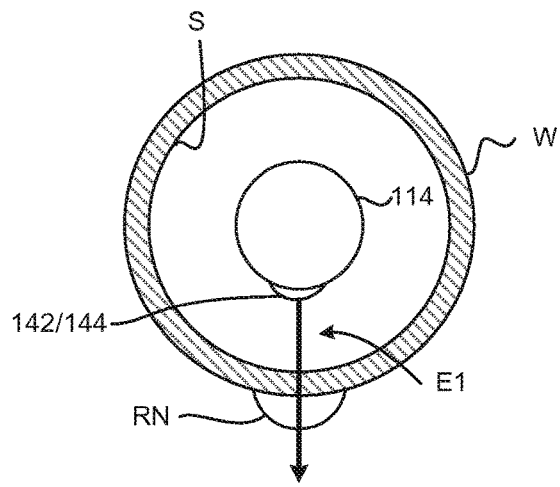
FIG. 2A is a schematic cross-sectional end view illustrating emission of energy toward a vessel wall from the transducer of FIG. 1 in accordance with an embodiment of the present technology.
Figure 2B:
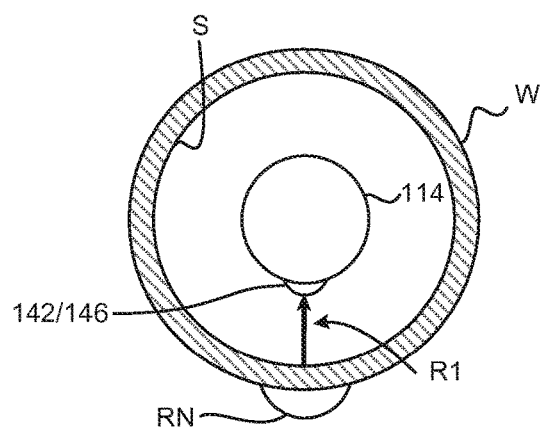
FIGS. 2B and 2C are schematic cross-sectional end views illustrating the reflected energy from the energy emission shown in FIG. 2A in accordance with an embodiment of the present technology.
Figure 2C:
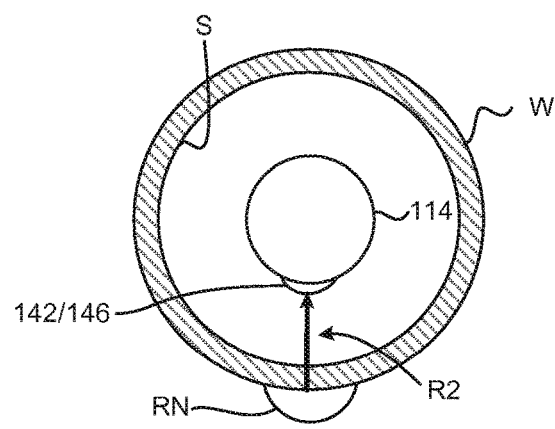

FIGS. 2A-2C are schematic cross-sectional end views showing the operation of one embodiment of a diagnostic ultrasound transducer 142 in accordance with an embodiment of the present technology. As shown, when activated manually by the clinician and/or automatically by the controller 138, the emitter 144 (of the transducer 142) can emit a diagnostic energy emission E1 toward tissue at least proximate to a wall (W) of the vessel or lumen (e.g., the renal artery). Depending on the physiological and anatomical parameters of each patient, a single diagnostic ultrasound emission can produce return energy in the form of countless reflections, individually corresponding to a unique reflecting surface. For example, almost instantaneously (e.g., within approximately 30 µs), the corresponding detector 146 of the transducer 142 can detect the return energy in the form of reflections or echoes of the first diagnostic ultrasound emission. As shown in FIG. 2B, an ultrasound reflection R1 can correspond to an interior surface (S) of the vessel wall (W). This is because an interior surface (S) of the vessel is often times the closest reflecting surface to the transducer 142 (and thus has the shortest response time). As shown in FIG. 2C, the emission E1 can also produce another, subsequent reflection R2 that can correspond to a nerve (e.g., a renal nerve (RN)). The second reflection R2 can be detected temporally after the first reflection R1 since the nerve (RN) is spatially farther from the diagnostic ultrasound transducer 142 than the interior surface (S) of the vessel wall (W).

Additionally or alternatively, the transducer 142 can be an electromagnetic transducer (not shown). The electromagnetic transducer 142 can emit electromagnetic energy (e.g., infrared, near infrared, visible, ultraviolet radiation, etc.) toward tissue at least proximate a wall of a renal vessel, or artery or another body lumen (e.g., the renal artery). Return energy, however, is measured by how much radiation is absorbed by the tissue and how much energy is reflected by the tissue back to the transducer 142 and/or detector 146. For example, at least a portion of the electromagnetic energy emitted by the emitter 144 of the electromagnetic transducer 142 can be absorbed by the vessel wall. The detector 146 then measures the return energy as the quantity of light not absorbed. As discussed in greater detail below, the return energy (e.g., ultrasound reflections and/or the amount of electromagnetic energy absorbed/not absorbed) may have varying parameters depending on type of tissue contacted by the emitted diagnostic energy. For example, neural tissue, smooth muscle tissue of the vessel wall, fat tissue, lymph node tissue, damaged tissue, and other local tissue individually exhibit different responses to diagnostic ultrasound and/or electromagnetic energy.

After detecting the return energy, the detector 146 and/or transducer 142 then convert the reflected energy to a signal, and transmits that signal to the controller 138 (FIG. 1). In some embodiments, the emitter 144 and detector 146 are continuously emitting/detecting energy and sending signals to the controller 138. Both the emitter 144 and the detector 146 can be operably coupled to the controller 138 within the console 106 via the connector 108 or wirelessly such that the console 106 may transmit a signal to the emitter 144 and receive signals from the detector 146 that correspond to the detected reflection R1. As described in further detail herein, the controller 138 and/or one or more diagnostic algorithms 134 can use the raw reflected signal and/or statistics based on the raw reflected signal (collectively referred to as a "parameters of the return energy") to provide positional and/or tissue characterization feedback to the clinician.

Non-exhaustive examples of the one or more parameters of return energy the controller 138 and/or diagnostic algorithms 134 may include an amplitude of the return energy, an average amplitude of the return energy, a minimum amplitude of the return energy, a maximum amplitude of the return energy, rate of change of amplitude, an amplitude at a predetermined or calculated time relative to a predetermined or calculated amplitude, a frequency of the return energy, an average frequency of the return energy, a minimum frequency of the return energy, a maximum frequency of the return energy, rate of change of frequency, a frequency at a predetermined or calculated time relative to a predetermined or calculated frequency, a change in time between the emission of energy and the detection of a return energy (referred to herein as a "detection time"), a detection time at a predetermined or calculated time relative to a predetermined or calculated detection time, change(s) in temperature over a specified time, a maximum temperature, a maximum average temperature, a minimum temperature, a temperature at a predetermined or calculated time relative to a predetermined or calculated temperature, an average temperature over a specified time, and other suitable measurements and/or derived statistics thereof.

III. Delivery Methods

Referring to FIG. 3, intravascular delivery of the treatment assembly 114 can include percutaneously inserting a guidewire (not shown) within the vasculature at an access site (e.g., femoral, brachial, radial, or axillary artery) and moving the shaft 116 and the treatment assembly 114 in a delivery state (e.g., generally straight, low-profile, etc.) along the guidewire until at least a portion of the treatment assembly 114 reaches the treatment location. In some embodiments, the shaft 116 and the treatment assembly 114 can include a guidewire lumen (not shown) configured to receive a guidewire in an over-the-wire or rapid exchange configuration. In some embodiments, the treatment assembly 114 may be delivered to a treatment site within a guide sheath (not shown) with or without using the guide wire. In other embodiments, the shaft 116 may be steerable itself such that the treatment assembly 114 may be delivered to the treatment site without the aid of the guidewire and/or guide sheath. As illustrated, the handle assembly 112 of the shaft 116 can be extracorporeally positioned and manipulated by the operator (e.g., via the actuator 122) to advance the shaft 116 through the sometimes tortuous intravascular path (P) and remotely manipulate the distal portion 118 of the shaft 116. Computed tomography (CT), fluoroscopy, intravascular ultrasound (IVUS), optical coherence tomography (OCT), or other suitable guidance modalities, or combinations thereof, may be used to aid the clinician's manipulation.

Further, in some embodiments, image guidance components (e.g., IVUS, OCT) may be incorporated into the treatment device 102 itself.

Once the treatment assembly 114 is positioned at a treatment location, the guidewire can be at least partially introduced (e.g., inserted) into or removed (e.g., withdrawn) from the treatment assembly 114 to transform or otherwise move the treatment assembly 114 to a deployed state. In cases where a guide sheath is used, the guide sheath can be at least partially removed (e.g., withdrawn) to transform the treatment assembly 114 into the deployed state (e.g., expanded, bent, deflected, helical and/or spiral, balloon, zig-zag, star-shaped, Malecot, etc.). For example, at least a portion of the treatment assembly 114 can have a shape memory corresponding to a deployed state and the sheath and/or guidewire can prevent the treatment assembly 114 from deploying in response to the shape memory before reaching the treatment location. In some embodiments, the treatment assembly 114 can be converted (e.g., placed or transformed) between the delivery and deployed states via remote actuation, e.g., using an actuator 122 (FIG. 1) of the handle assembly 112. The actuator 122 can include a knob, a pin, a lever, a button, a dial, or another suitable control component.

In the deployed state, the treatment assembly 114 can be configured to contact an inner wall of the vessel (e.g., the renal artery) and to cause a fully-circumferential lesion without the need for repositioning. For example, the treatment assembly 114 can be configured to form a lesion or series of lesions (e.g., a helical/spiral lesion or a discontinuous lesion) that is fully-circumferential overall, but generally non-circumferential at longitudinal segments of the treatment location. This can facilitate precise and efficient treatment with a low possibility of vessel stenosis. In other embodiments, the treatment assembly 114 can be configured to form a partially-circumferential lesion or a fully-circumferential lesion at a single longitudinal segment of the treatment location. During treatment, the treatment assembly 114 can be configured to partially or fully occlude the vessel (e.g., the renal artery). Partial occlusion can be useful, for example, to reduce renal ischemia, and full occlusion can be useful, for example, to reduce interference (e.g., warming or cooling) caused by blood flow through the treatment location. In some embodiments, the treatment assembly 114 can be configured to cause therapeutically-effective neuromodulation (e.g., using ultrasound energy) without contacting a vessel wall.

Examples of other suitable neuromodulation delivery configurations, deployment configurations and/or deployment mechanisms can be found in U.S. application Ser. No. 12/910,631, filed Oct. 22, 2010, entitled "APPARATUS, SYSTEMS, AND METHODS FOR ACHIEVING INTRAVASCULAR, THERMALLY-INDUCED RENAL NEUROMODULATION," U.S. application Ser. No. 13/281,361, filed Oct. 25, 2011, entitled "CATHETER APPARATUSES HAVING MULTI-ELECTRODE ARRAYS FOR RENAL NEUROMODULATION AND ASSOCIATED SYSTEMS AND METHODS," and U.S. Provisional Application No. 61/646,218, filed May 5, 2012, entitled "MULTI-ELECTRODE CATHETER ASSEMBLIES FOR RENAL NEUROMODULATION AND ASSOCIATED SYSTEMS AND METHODS," which are incorporated herein by reference in their entireties.

IV. Control of Applied Energy

A. Power Delivery

Figure 4A:
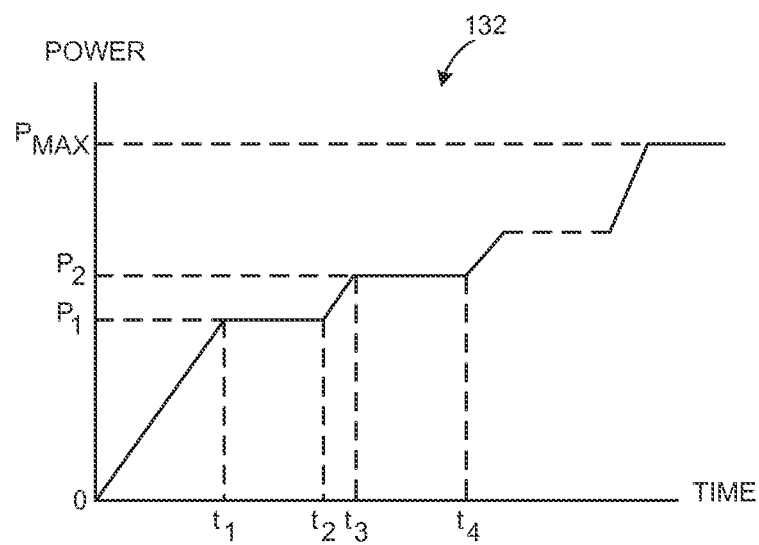
FIG. 4A is a graph depicting an energy delivery algorithm that may be used in conjunction with the system of FIG. 1 in accordance with an embodiment of the technology.

As mentioned above, the console 106 can be configured to deliver the neuromodulation energy (e.g., RF energy) via an automated control algorithm 132 and/or under the control of a clinician. FIG. 4A shows one embodiment of an automated control algorithm 132 that may be implemented by the controller 138 coupled to the console 106. As seen in FIG. 4A, when a clinician initiates treatment (e.g., via the foot pedal 136 illustrated in FIG. 1), the control algorithm 132 can include instructions that cause the console 106 to gradually adjust the power output to a first power level $P_1$ (e.g., 5 watts) over a first time period $t_1$ (e.g., 15 seconds). The power can increase generally linearly during the first time period. As a result, the console 106 increases its power output at a generally constant rate of $P_1/t_1$. Alternatively, the power may increase non-linearly (e.g., exponential or parabolic) with a variable rate of increase. Once $P_1$ and $t_1$ are achieved, the algorithm may hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3-t_2$ (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 6.5 watts. Optionally, the power may be maintained at the maximum power $P_{MAX}$ for a desired period of time or up to the desired total treatment time (e.g., up to about 120 seconds).

Furthermore, the control algorithm 132 includes monitoring one or more of the temperature, time, impedance, power, flow velocity, volumetric flow rate, blood pressure, heart rate, parameters of return energy, or other operating parameters. The operating parameters may be monitored continuously or periodically. The control algorithm 132 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment may continue at the commanded power output. If monitored parameters fall outside the ranges set by the predetermined parameter profiles, the control algorithm 132 adjusts the commanded power output accordingly. For example, if a measured temperature threshold (e.g., 65° C.) is achieved, then power delivery is kept constant until the total treatment time (e.g., 120 seconds) has expired. If a first temperature threshold (e.g., 70° C.) is achieved or exceeded, then power is reduced in predetermined increments (e.g., 0.5 watts, 1.0 watts, etc.) until the measured temperature drops below the first temperature threshold. If a second temperature threshold (e.g., 85° C.) is achieved or exceeded, thereby indicating an undesirable condition, then power delivery may be terminated. The system may be equipped with various audible and visual alarms to alert the operator of certain conditions.

B. Synchronization of Sensing and Power Delivery

Figure 4B:
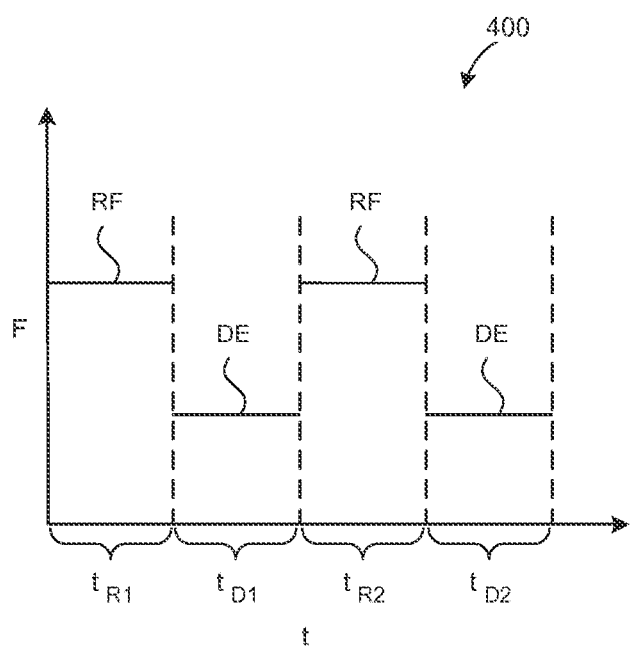
FIG. 4B is a graph depicting a synchronization algorithm that may be used in conjunction with the energy delivery algorithm of FIG. 4A in accordance with an embodiment of the present technology.

At one or more timepoints during and/or after delivering the therapeutic energy, the transducer 142 can be activated to provide feedback as to the efficacy of the ongoing or completed therapeutic energy delivery. The transducer 142 can be activated automatically by the controller 138 or manually by the clinician. The transducer 142 can emit energy and detect a return energy continuously, at set intervals, and/or at one or more discrete timepoints that are selected automatically or by the clinician. When RF energy is used to modulate the nerves, the console 106 and/or controller 138 can run a synchronizing algorithm 400 that avoids interference between the RF signals to the neuromodulation element 140 (e.g., ≥100 KHz) and the signals to the transducer 142 (e.g., 20-40 MHz). As shown in FIG. 4B, the energy transmission to the neuromodulation element 140 (RF) and the timing of energy transmission to the transducer 142 (DE) can be time-multiplexed by the synchronizing algorithm 400 such that RF energy (RF) and diagnostic energy (DE) are activated at different time periods. For example, the RF and DE duty cycles can be alternatingly activated (e.g., RF on/off, DE on/off, RF on/off, DE on/off, etc.). The transducer 142 can accordingly emit energy from the assembly toward the tissue while modulating the renal nerve and/or intermittently between modulating the renal nerve. Furthermore, the time RF remains on ($t_{R1}$) and the time DE remains on ($t_{U1}$) can be the same (e.g., 25 µs) or different. In these and other embodiments, a filter may be used on the raw signal of the return energy to remove RF interference. One, a few, or all of the above techniques may be utilized.

V. Pre-Neuromodulation Evaluation

With the treatments disclosed herein for delivering therapeutic energy to target tissue, it may be beneficial to evaluate a relative position of at least a portion of the treatment assembly 114 before delivering the therapeutic energy. Contact between the energy delivery element and the tissue, nerve alignment, and nerve proximity are all factors that can affect the efficacy of the neuromodulation. Accordingly, one or more transducers 142 carried by the treatment assembly 114 can be configured to emit energy towards the vessel wall and send information regarding a detected return energy of the emission to the controller 138. As discussed in greater detail below, the controller 138 can execute one or more diagnostic algorithms 134 that can inform a clinician of a position of at least a portion of the treatment assembly 114 relative to a vessel wall and/or a nerve (e.g., a renal nerve).

A. Feedback Related to Tissue Contact

The quality and/or success of the purposeful application of energy depends at least in part on having good contact between the energy delivery element and the tissue at a desired target site. If the contact between the energy delivery element and the tissue is insufficient, the energy delivery is more likely to be therapeutically ineffective. For example, insufficient contact can cause under-ablation, over-ablation, inadequate lesion formation, premature high impedance shut-off, etc. Accordingly, it is often important to determine whether there is adequate tissue contact before delivering energy. Many clinicians currently use a combination of tactile feedback, imaging devices, and/or other qualitative measures to assess tissue contact, but these measures often do not accurately determine electrode-tissue contact. For example, intracardiac echocardiography provides a real-time image of the anatomy surrounding the distal portion of an ablation catheter, but it does not give an objective assessment of electrode-tissue contact, nor does it have sufficient contrast to visualize the formation of created lesions (e.g., 2D images of a 3D surface).

Figure 5:
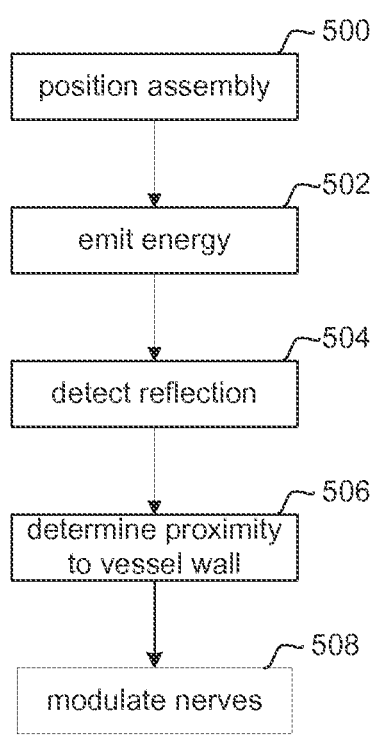
FIG. 5 is a block diagram illustrating stages of a method for operating the system shown in FIG. 1 in accordance with an embodiment of the present technology.

FIG. 5 is a block diagram illustrating stages of a method for operation of the system 100 in accordance with an embodiment of the present technology. The method can include positioning the treatment assembly 114 within or at least proximate to a renal vessel or other body lumen of a human (block 500). The emitter 144 can then be activated automatically by a control algorithm or manually activated by the operator to emit energy towards tissue at or at least proximate to a wall of the renal vessel or other body lumen (block 502). A return energy of the emitted energy can be detected by a detector 146 (block 504) that communicates a signal to the controller.

Figure 6A:
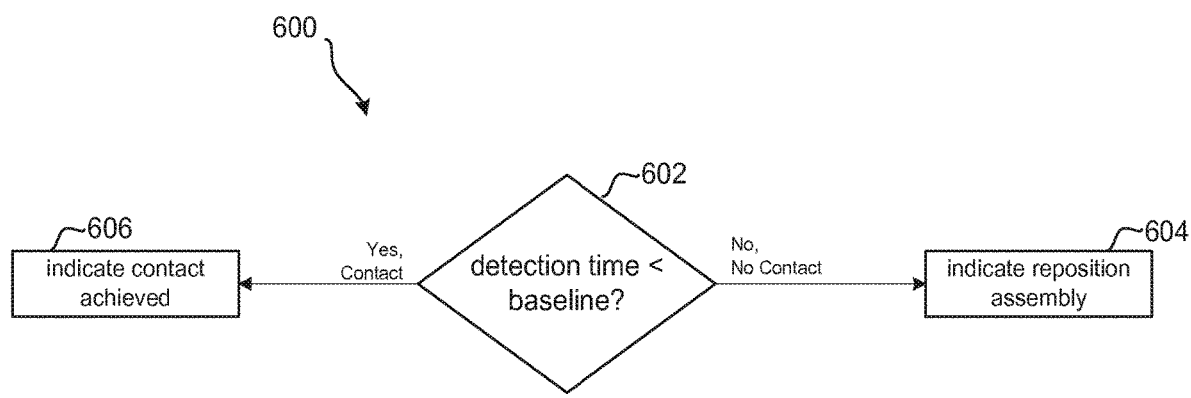
FIG. 6A is a block diagram illustrating an algorithm for providing operator feedback regarding contact between the energy delivery element and the tissue in accordance with an embodiment of the present technology.
Figure 6B:
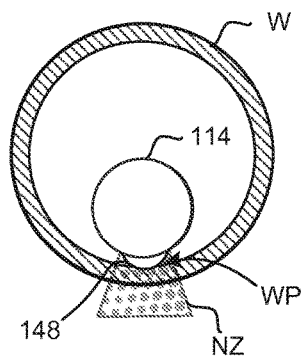
FIGS. 6B-6E are schematic cross-sectional end views illustrating a wall proximity of the treatment assembly to a vessel wall in accordance with an embodiment of the present technology.
Figure 6C:
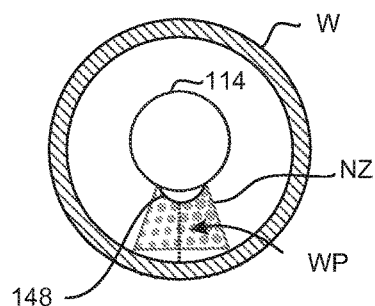
Figure 6D:
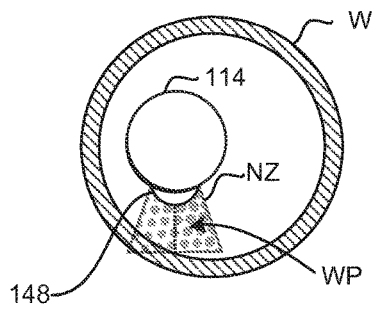
Figure 6E:
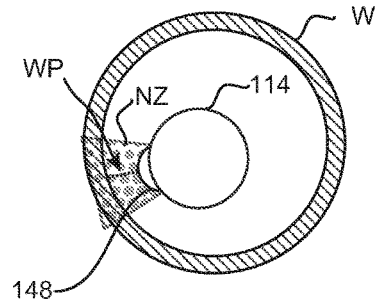

The method can continue by determining the proximity of the treatment assembly 114 to the vessel wall which can be determined based on the detected return energy (block 506). FIG. 6A is a block diagram of one embodiment of a diagnostic algorithm 600 configured in accordance with the present technology. The diagnostic algorithm 600 can determine a wall proximity of at least a portion of the treatment assembly 114 to the vessel wall based on one or more parameters of return energy (e.g., the raw reflected signal and/or statistics based on the raw reflected signal including detection time and signal amplitude). As shown in the schematic cross-sectional end views of FIGS. 6B-6E, an energy delivery element 148 can deliver energy within a particular zone or region (referred to herein as a "neuromodulation zone (NZ)"). As shown, "wall proximity (WP)" refers to the distance between a particular energy delivery element 148 and the inner surface of the vessel wall (W) in the direction of energy delivery and/or within the neuromodulation zone (NZ). The wall proximity (WP) can be calculated as an actual distance (e.g., 7 microns) or a relative distance (e.g., not close enough contact, etc.). Accordingly, the wall proximity (WP) can be the distance between the energy delivery element 148 and wall (W) within the neuromodulation zone (NZ). When the energy delivery element 148 is in contact with the vessel wall (W), as shown in FIG. 6B, the wall proximity (WP) is very small. Likewise, the wall proximity (WP) is larger than that of FIG. 6B when the energy delivery element 148 is spaced apart from the vessel wall (W), as shown in FIGS. 6C-6E.

Determining the relative position of the energy delivery element 148 to the vessel wall (VW) based on the return energy detected by the transducer 142 is possible so long as the transducer 142 and the corresponding energy delivery element 148 are fixedly positioned on the treatment assembly 114 relative to each other. In other words, the diagnostic algorithms 134 discussed herein can take into account the relative position of the transducer(s) 142 and energy delivery elements 148 and normalize the resulting proximity determinations accordingly.

Referring to FIGS. 6A-6E together, the diagnostic algorithm 600 can determine a wall proximity (WP) of at least a portion of the treatment assembly 114 to the vessel wall (W) based on, inter alia, a parameter of return energy such as detection time (e.g., a change in time between the emission of energy and the detection of the return energy). As shown in decision block 602, the algorithm 600 can compare the detection time to a baseline detection time. The baseline detection time can take into account the power delivery schedule, time, blood flow through the vessel, biological parameters of the individual patient and/or a particular subset of patients, and other suitable criteria. In embodiments having two or more transducers 142, the controller 138 can execute the algorithm 600 simultaneously for all of the transducers 142, or at different time periods using multi-plexing for each transducer 142 individually or groups of transducers 142. For example, a clinician may only desire to check the contact and/or wall proximity (WP) of one of the energy delivery elements in an array having a plurality of energy delivery elements. The clinician can selectively run the algorithm 600 on the transducer 142 corresponding to the energy delivery element in question. In some embodiments, the controller 138 may automatically select which energy delivery element to test and automatically activate the transducer to determine the proximity of the energy delivery element(s) to the vessel wall (W). For example, the controller 138 can select all of the energy delivery elements serially or certain subsets of the energy delivery elements to be tested. In some embodiments, the detection time can be indicated by the console 106 (e.g., via the indicator 126) and manually compared to a baseline detection time by the clinician.

Depending on the result of decision block 602, the controller 138 can cause an indicator to notify the clinician whether to reposition the treatment assembly 114 (block 604) or begin energy delivery (block 606). For example, if the detection time within a desired range, the contact between the energy delivery element 148 and the vessel wall (W) is sufficient for treatment (see FIG. 6D-6F). The desired range can have a maximum detection time setting an upper limit, a minimum detection time setting a non-zero lower limit and a maximum detection time setting an upper limit, or a mid-point and an acceptable margin around the mid-point. In this case, the controller 138 can cause the indicator to notify the clinician of sufficient tissue contact and to begin energy delivery. Notifications of sufficient electrode-tissue contact can include messages on the display 126 of the console 106 such as "Contact Achieved," a green light, or similar notifications. Likewise, the console 106 can indicate sufficient electrode-tissue contact through one or more lights on the console 106 and/or handle assembly 112 of the treatment device 102.

If the detection time is not in the desired range, the controller can cause the indicator to display insufficient electrode-tissue contact and the clinician can reposition the treatment assembly 114. Indications of insufficient electrode-tissue contact can include messages on the display 126 of the console 106 such as "Insufficient Contact," "Reposition Catheter," a red light, or other notifications. If the treatment assembly 114 is repositioned, stages 502-506 (FIG. 5) can be repeated to ensure sufficient electrode-tissue contact is achieved. The method can continue by delivering energy through the neuromodulation element 140 of the treatment assembly 114 to modulate the nerves (block 508).

The detection time may be greater than the baseline detection time due to chronic instability of at least a portion of the treatment assembly 114 instead of inadequate positioning of the treatment assembly 114 or energy delivery element 148. In these and other embodiments, the controller may further include an algorithm configured to assess such chronic instabilities in conjunction with one or more of the control and/or diagnostic algorithms disclosed herein. Such suitable algorithms are disclosed in U.S. application Ser. No. 13/281,269, filed Oct. 25, 2011, entitled "DEVICES, SYSTEMS, AND METHODS FOR EVALUATION AND FEEDBACK OF NEUROMODULATION TREATMENT," and U.S. application [Reference No. C3171.USU1], entitled "DEVICES, SYSTEMS, AND METHODS FOR EVALUATION AND FEEDBACK OF NEUROMODULATION TREATMENT," filed Mar. 15, 2013, are incorporated herein by reference in their entireties.

B. Feedback Related to Positioning

Several aspects of the present technology that are directed to determining the proximity of at least a portion of the treatment assembly 114 to the renal nerve (RN) can also be used to enhance the efficacy of treatment. For example, the neuromodulation element 140 of the treatment assembly 114 can be more accurately aligned with renal nerve(s) (RN) such that the energy is more consistently delivered to the renal nerves (RN) instead of smooth muscle tissue of the vessel where there is little or no neural tissue. This may provide for more consistent ablation or other neuromodulation of the renal nerves (RN), reduce or otherwise modify the power delivery, and/or enhance control of other parameters of the control algorithm 132.

Without being bound by theory, it is believed that the amplitude and frequency of the detected return energy can depend in part on the types of tissue through which the diagnostic energy propagates. For example, referring to FIG. 7B, since muscle tissue (e.g., the vessel wall) will reflect a greater portion of ultrasound energy than does nerve tissue, it is expected that detected return energy 710 corresponding to muscle tissue will generally have a greater amplitude than that of detected return energy corresponding to nerve tissue. In one embodiment, the difference in amplitude between the detected return energy 710 from the muscle and the detected return energy 708 from nerves is at least approximately 10 dB. Similarly, it is believed that the frequencies of the detected return energy of muscle tissue and nerve tissue are different. Signal characterization, for example, could be determined using empirical data from animal studies. For example, return energy data could be collected in known anatomical locations and the histology of the tissue could then be correlated to the return energy data to characterize signals according to the type of reflecting tissue.

Figure 7A:
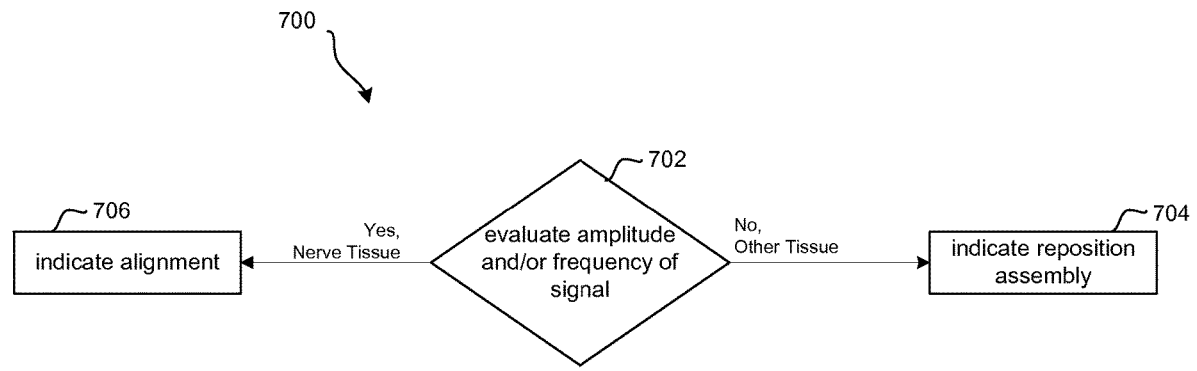
FIG. 7A is a block diagram illustrating an algorithm for providing operator feedback regarding circumferential proximity in accordance with an embodiment of the present technology.
Figure 7B:
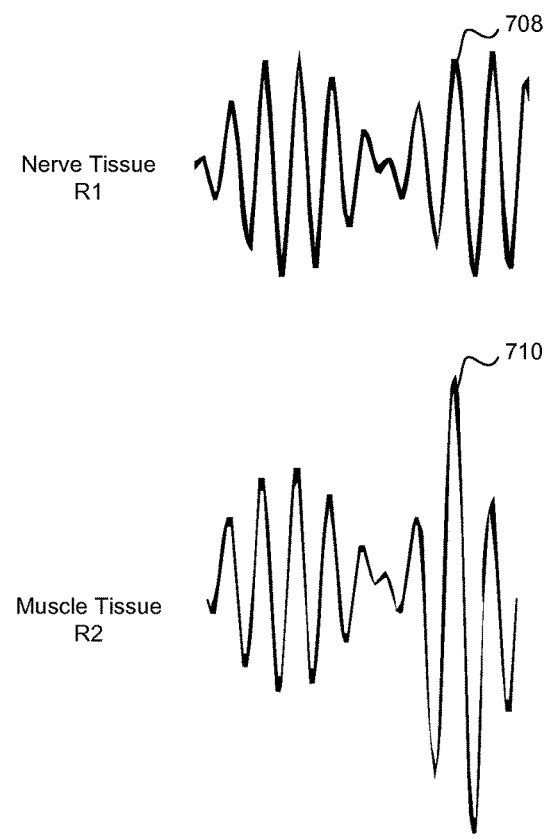
FIG. 7B is a graph depicting a parameter of return energy sensed by the system of FIG. 1 in accordance with an embodiment of the technology.
Figure 7C:
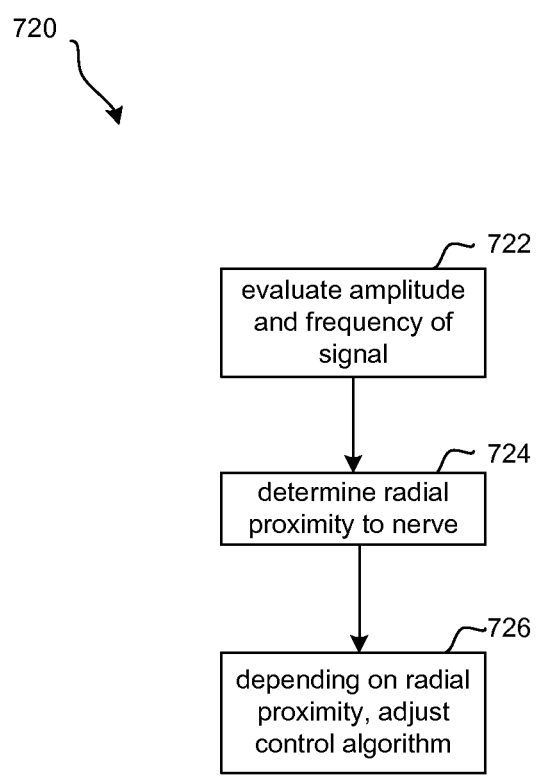
FIG. 7C is a block diagram illustrating an algorithm for providing operator feedback regarding radial proximity in accordance with an embodiment of the present technology.
Figure 7D:
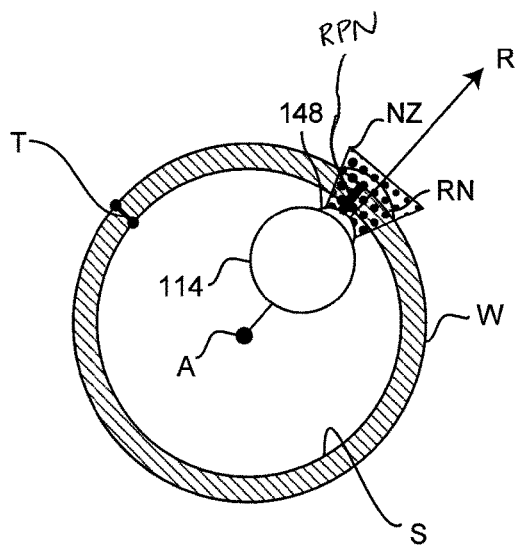
FIGS. 7D-7F are schematic cross-sectional end views illustrating radial and/or circumferential proximities of the treatment assembly to a nerve in accordance with an embodiment of the present technology.
Figure 7E:
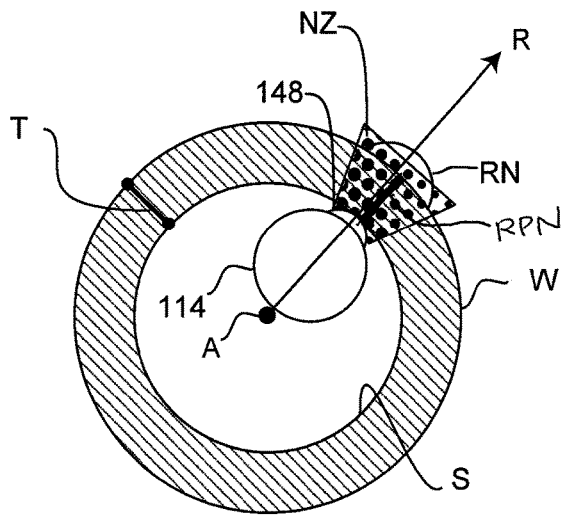
Figure 7F:
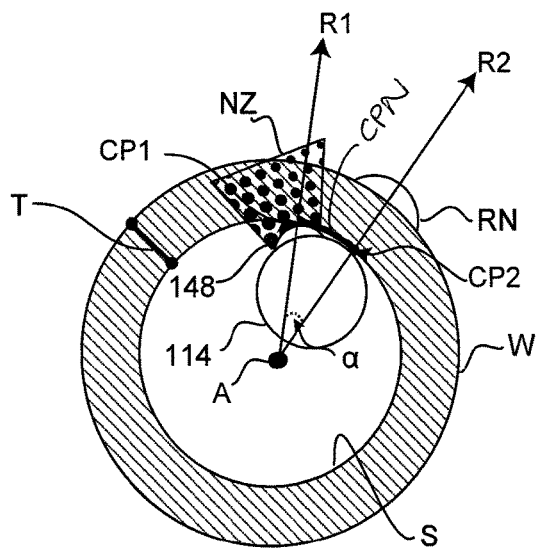

FIGS. 7D-7F are schematic, cross-sectional end views of a vessel showing various proximities of the treatment assembly 114 and/or one or more energy delivery elements 148. FIG. 7C is a block diagram of one embodiment of a diagnostic algorithm 720 configured in accordance with the present technology that can determine a radial proximity (RPN) of at least a portion of the treatment assembly 114 to a target nerve (e.g., renal nerve) based on one or more parameters of return energy such as the amplitude and frequency (and/or derivations thereof) of the detected return energy. As shown in FIGS. 7D and 7E, "radial proximity (RPN)" refers to the distance between a particular energy delivery element 148 and the renal nerve (RN) in the direction of energy delivery and/or within the neuromodulation zone (NZ) along a radian (R) relative to a central axis (A) of the blood vessel. The radial proximity (RPN) can be calculated as an actual distance (e.g., 7 microns) or a relative distance from the energy delivery element 148 to the renal nerve (RN) (e.g., the nerve (RN) is deep within the wall (W), the nerve (RN) is close to the interior surface of the wall (W), etc.). Depending on the thickness (T) of the vessel wall (W), position of the nerve (RN) within and/or on the adventitia, and others parameters, the radial proximity (RPN) can be relatively small (FIG. 7E), relatively large (FIG. 7D), or other gradations in between (block 724). The diagnostic algorithm 700 can evaluate the amplitude and/or frequency of the detected return energy (block 722) and cause, for example, the controller 138 to adjust and/or modify the power delivery control algorithm 132 to compensate for the radial proximity (RPN) of the energy delivery element 148 to the nerve (RN) (block 726). For example, if the diagnostic algorithm 700 evaluates the raw signal of the detected return energy and determines a renal nerve (RN) is radially closer than predicted (block 724), the controller 138 can decrease $P_{MAX}$ and/or $t_1$, $t_2$, $t_3$, etc. of the power-control algorithm 132. In some embodiments, the duty cycle, frequency, or other parameters of the power-control algorithm can be modified.

In some embodiments, if the parameter of return energy (e.g., amplitude or frequency) is outside of a predetermined range, the controller 138 can cause the indicator to indicate the radial proximity (RPN) and automatically adjust and/or modify the power-control algorithm 132. The predetermined range can have a selected minimum or maximum threshold value that set a floor or ceiling, a minimum a non-zero lower limit and a maximum upper limit that set a floor and a ceiling, or a mid-point and an acceptable margin around the midpoint. In one embodiment, the indicator can provide a message that the nerve is closer than expected when the radial proximity (RPN) value is low or that the nerve is deeper than expected when the radial proximity (RPN) value is high. In some embodiments, the clinician can manually adjust the power-control algorithm. If the parameter of return energy is within a predetermined threshold, the controller 138 can cause the indicator to indicate the radial proximity (RPN) is suitable (e.g., the nerve is within a desired distance and alignment with the energy delivery element 148). At this point, the clinician can begin neuromodulation, or alternatively, the clinician can continue to check other relative positions of the treatment assembly 114.

FIG. 7A is a block diagram of one embodiment of a diagnostic algorithm 700 configured in accordance with the present technology that can determine a circumferential proximity (CPN) of at least a portion of the treatment assembly 114 to a target nerve (e.g., renal nerve) based on one or more parameters of return energy such as the amplitude and frequency (and/or derivations thereof) of the detected return energy. FIGS. 7D and 7F show examples of "circumferential proximity (CPN)," which refers to the distance along the circumference of the inner wall (S) of the blood vessel between the location of the energy delivery element 148 and a location at the inner wall (S) directly opposite a renal nerve (RN). For example, in FIG. 7F, the energy delivery element 148 has a circumferential position CP1 and the nerve (RN) has a circumferential position CP2. The circumferential proximity (CPN) can be the angle α between radians R1 and R2 passing through circumferential positions CP1 and CP2, or the distance along the circumference of the inner wall (W) of the vessel between circumferential positions CP1 and CP2. If evaluation of the amplitude and/or frequency shows the value of the circumferential proximity (CPN) is above a selected value (block 702), the energy delivery element 148 and the nerve (RN) are not adequately aligned circumferentially (FIG. 7F). In such cases, at least a portion of the treatment assembly 114 can be repositioned to better align the energy delivery element 148 with the nerve (RN) (FIG. 7D) (block 704).

In some embodiments, if the parameter of return energy (e.g., amplitude or frequency) is outside of a predetermined range the controller 138 can cause the indicator to indicate the circumferential proximity (CPN) and automatically adjust and/or modify the power control algorithm 132. The predetermined range can have a selected minimum or maximum threshold value that set a floor or ceiling, a minimum a non-zero lower limit and a maximum upper limit that set a floor and a ceiling, or a mid-point and an acceptable margin around the midpoint. In one embodiment, the indicator can provide a message that the energy delivery element(s) 148 of the treatment assembly 114 are not adequately circumferentially aligned with the renal nerve when the circumferential proximity (CPN) value is high. The indicator can further instruct the clinician to reposition the treatment assembly 114. In some embodiments, the controller 138 can automatically cause a motorized transducer to rotate the energy delivery element(s) 148 so as to be in proper alignment. If the parameter of return energy is within a predetermined threshold, the controller 138 can cause the indicator to indicate alignment. At this point, the clinician can begin neuromodulation, or alternatively, the clinician can continue to check other relative positions of the treatment assembly 114.

VI. Evaluation During or After Delivering Energy for Neuromodulation

A. Feedback Related to Tissue Characterization

Figure 8A:
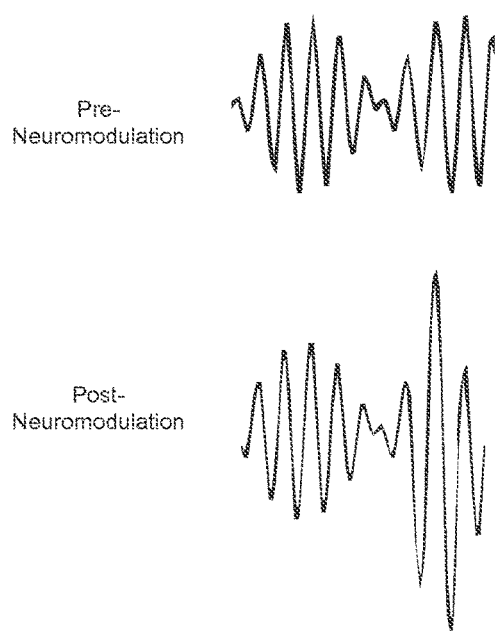
FIGS. 8A-8C are graphs depicting a parameter of return energy sensed by the system of FIG. 1 in accordance with an embodiment of the present technology.
Figure 8B:
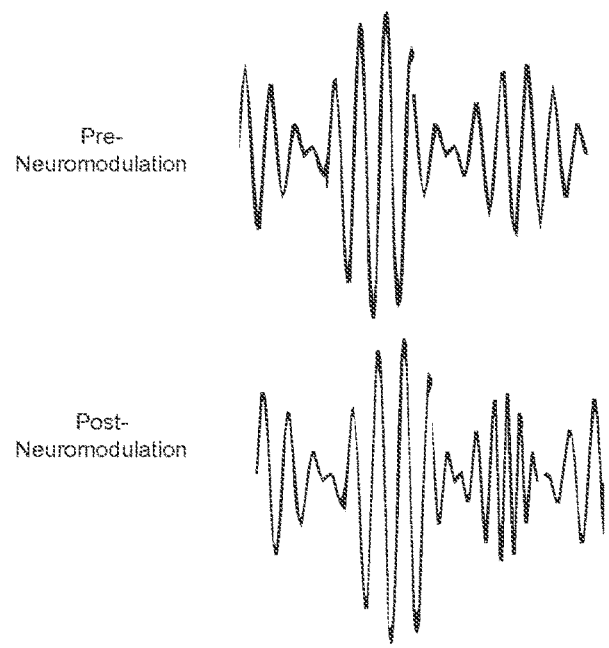
Figure 8C:
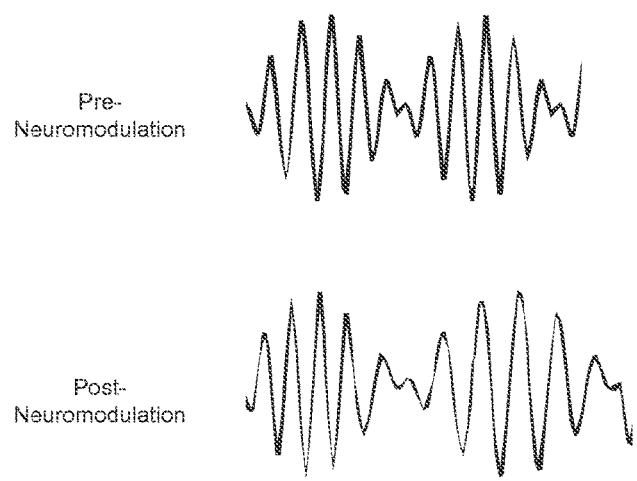

Similar to the disclosure with reference to FIGS. 7A-7E above, it is believed that the reflection or absorption of ultrasound, electromagnetic energy or other diagnostic energies from adequately neuromodulated (e.g., ablated) tissue are different than those of non-neuromodulated or under-neuromodulated tissue (e.g., non- or under-ablated). As a result, the parameters of the detected return energy, such as the amplitude, frequency and/or derivations of these parameters, can be used to indicate the extent of ablation or other alteration of the neural tissue. For example, FIG. 8A shows that the amplitude of the signal corresponding to the detected return energy before neuromodulation can be different (e.g., smaller) than the signal corresponding to the detected return energy after neuromodulation. FIGS. 8B and 8C show that the frequency of the signal corresponding to the detected return energy pre-neuromodulation can be different than the frequency of the signal corresponding to the detected return energy post-neuromodulation. For example, the pre-neuromodulation frequency is lower than the post-neuromodulation frequency in FIG. 8B, while the pre-neuromodulation frequency is higher than the post-neuromodulation frequency in FIG. 8C.

Accordingly, disclosed herein are one or more diagnostic algorithms that can use the raw signal corresponding to the detected return energy to characterize tissue at or at least proximate to a wall of a vessel (e.g., a renal artery). The diagnostic algorithm can characterize tissue based on one or more parameters of return energy to provide meaningful, real-time or relatively contemporaneous feedback to the clinician regarding the efficacy of the ongoing and/or completed energy delivery while the patient is still catheterized.

Figure 9:
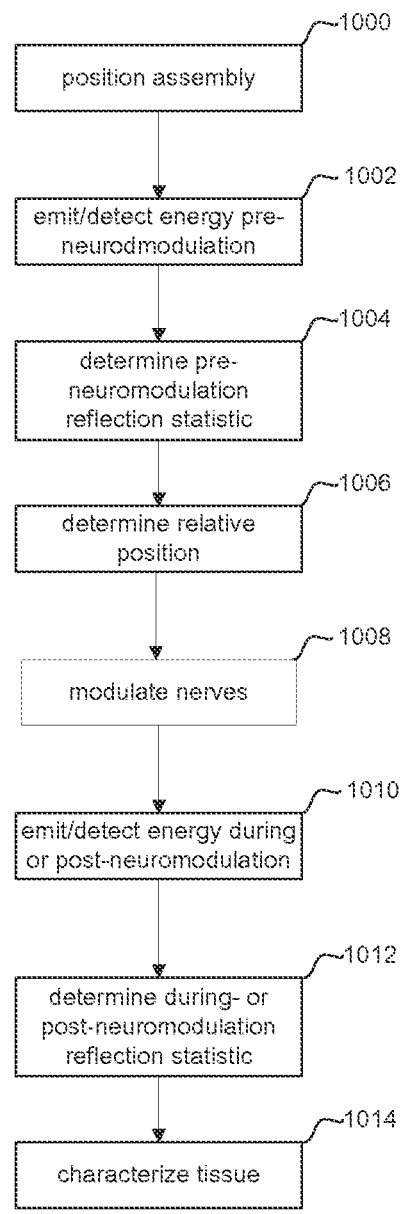
FIG. 9 is a block diagram illustrating stages during operation of the system shown in FIG. 1 in accordance with an embodiment of the present technology.

FIG. 9 is a block diagram illustrating stages of a method for operating the system 100 in accordance with an embodiment of the present technology. Blocks 1000-1008 are similar to the blocks 500-508 described above with reference to FIG. 5, however blocks 1000-1006 are performed before applying energy to the target area (e.g., pre-neuromodulation). During these pre-neuromodulation stages, the pre-neuromodulation parameters of return energy can be determined according to the methods and algorithms discussed above with reference to FIGS. 2-7E and stored in the memory of the controller 138. While modulating the nerves via energy delivery (block 1008) and/or after terminating energy delivery, the transducer 142 can emit energy and detect a return energy automatically by the controller 138 or manually by the clinician (block 1010). The diagnostic algorithm 1000 can determine one or more parameters of return energy during or after neuromodulation based on the detected return energy (block 1012). The diagnostic algorithm 1000 can then compare and/or evaluate the post-neuromodulation parameters of return energy in view of the pre-neuromodulation parameters of return energy to characterize the tissue (block 1014). The controller 138 can then cause the indicator to provide a characterization to the clinician and/or suggest a course of action, such as adjust the power-delivery control algorithm, terminate modulation, continue modulation, reposition, and other suitable choices.

B. Feedback Related to Vessel Wall Temperature

As mentioned above, it is believed that the reflected energy associated with a diagnostic ultrasound energy emission can vary depending on the properties of the reflecting surface (e.g., tissue). During a neuromodulation treatment, the temperature of the tissue at the vessel wall increases as energy is delivered to the tissue. This increase in temperature alters and/or affects the reflective properties of the tissue such as the ability of the tissue to conduct sound. For example, as the temperature of the tissue is increases, the speed of sound propagating through the tissue can increase. As a result, the time it takes to detect a reflection of emitted diagnostic ultrasound energy decreases as the temperature of the tissue increases. Accordingly, disclosed herein are one or more diagnostic algorithms that can use the raw signal corresponding to the detected reflection of a diagnostic ultrasound emission to determine the temperature of the vessel wall tissue (e.g. a renal artery) at a treatment site.

Figure 10A:
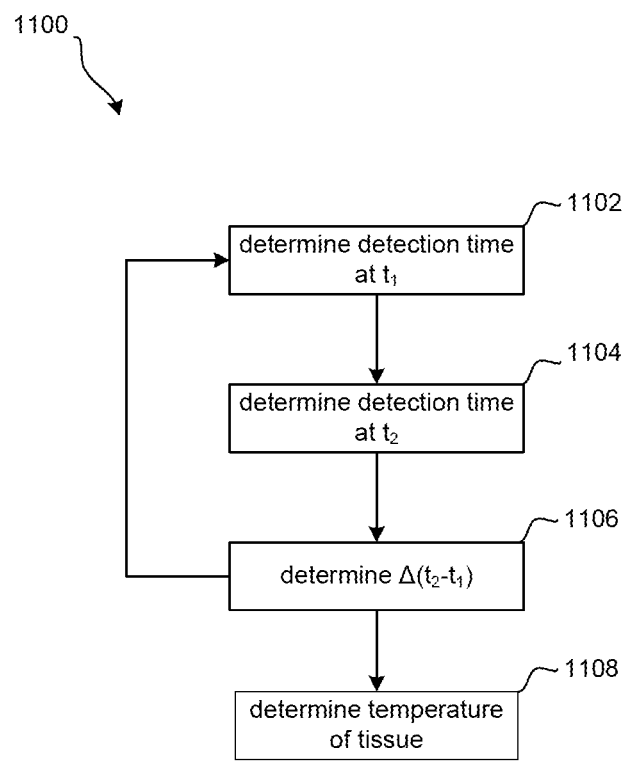
FIG. 10A is a block diagram illustrating an algorithm for providing operator feedback regarding tissue temperature at a vessel wall in accordance with an embodiment of the present technology.
Figure 10B:
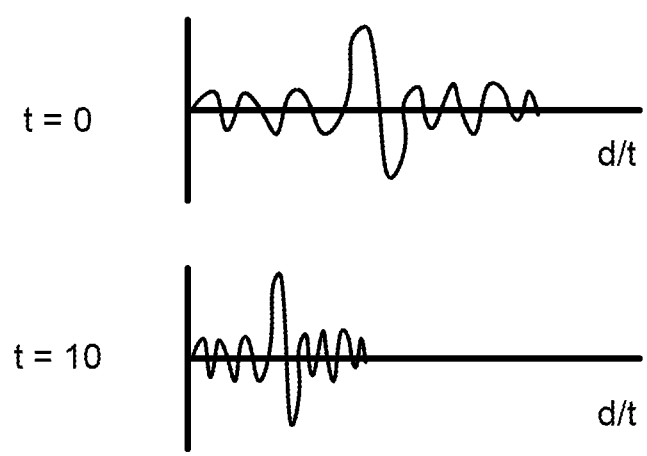
FIG. 10B is a graph depicting a parameter of return energy sensed by the system of FIG. 1 in accordance with an embodiment of the present technology.

For example, FIG. 10 is a block diagram of one embodiment of a diagnostic algorithm 700 configured in accordance with the present technology that can determine the temperature of the tissue based on one or more parameters of return energy such as the detection time, amplitude, and/or frequency (and/or derivations thereof) of the detected return energy. As shown, the diagnostic algorithm 1100 can determine a detection time of the return energy at two sequential time points (i.e., at a first time (block 1102) and a second time (block 1104)). The diagnostic algorithm 1100 can then determine a difference in the detection times (block 1106) and repeat this process (blocks 1102-1104) over a longer time interval. The longer time interval could correspond to a portion of a neuromodulation treatment or an entire neuromodulation treatment. Likewise, one or more longer time intervals can be evaluated for a given treatment or portion of a treatment. For example, as shown in FIG. 10B, at a time t=0, the amplitude has a first value. At time t=10 second, the amplitude can have a different value. The distance between these two peaks can be tracked over time and correlated to temperature of the tissue.

Using the difference in detection time between one or more sets of sequential time points, the diagnostic algorithm 1100 can determine a vessel wall temperature gradient in the direction of energy delivery (block 1108). For example, the temperature gradient may show different temperature values as the depth of the wall increases radially. In some embodiments, the diagnostic algorithm 1100 can correlate the detection time data to other parameters of return energy, such as amplitude and/or frequency, to enhance the accuracy and/or interpretation of the temperature gradient. Furthermore, the tissue temperature of the vessel wall at increasing radial depths can also inform a clinician of the degree of tissue damage and/or lesion depth. Current neuromodulation systems measure temperature through a temperature sensor (e.g., thermocouple, thermistor, etc.) positioned in or near the energy delivery element and thus are unable to gauge temperature across a vessel wall since. Such sensors are limited to temperature measurements at or near the interior surface of the vessel wall and can be inaccurate due to variations in blood flow and the degree of contact between the energy delivery element and the vessel wall.

VII. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 11:
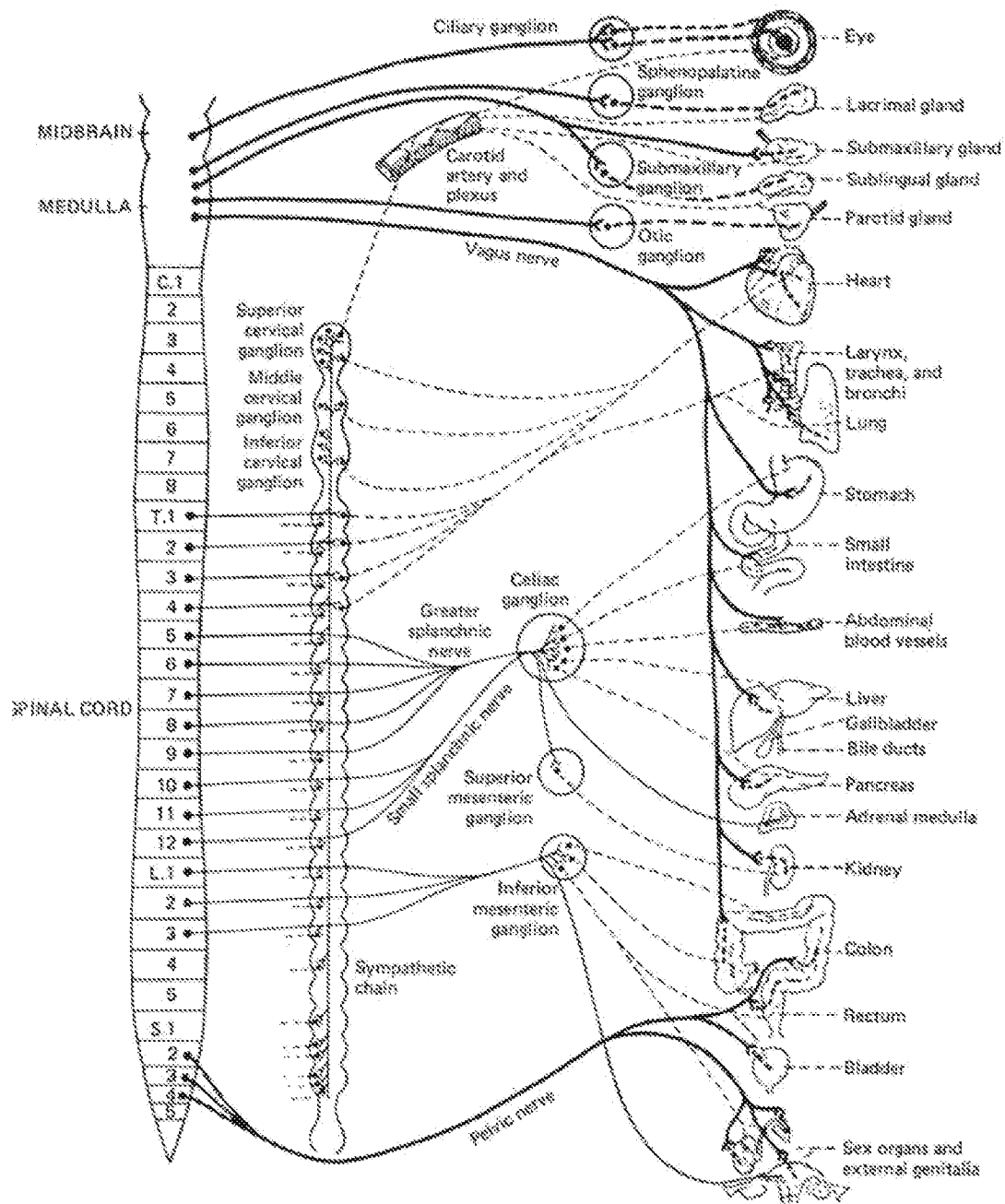
FIG. 11 is a conceptual diagram illustrating the sympathetic nervous system and how the brain communicates with the body via the sympathetic nervous system.

As shown in FIG. 11, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 12:
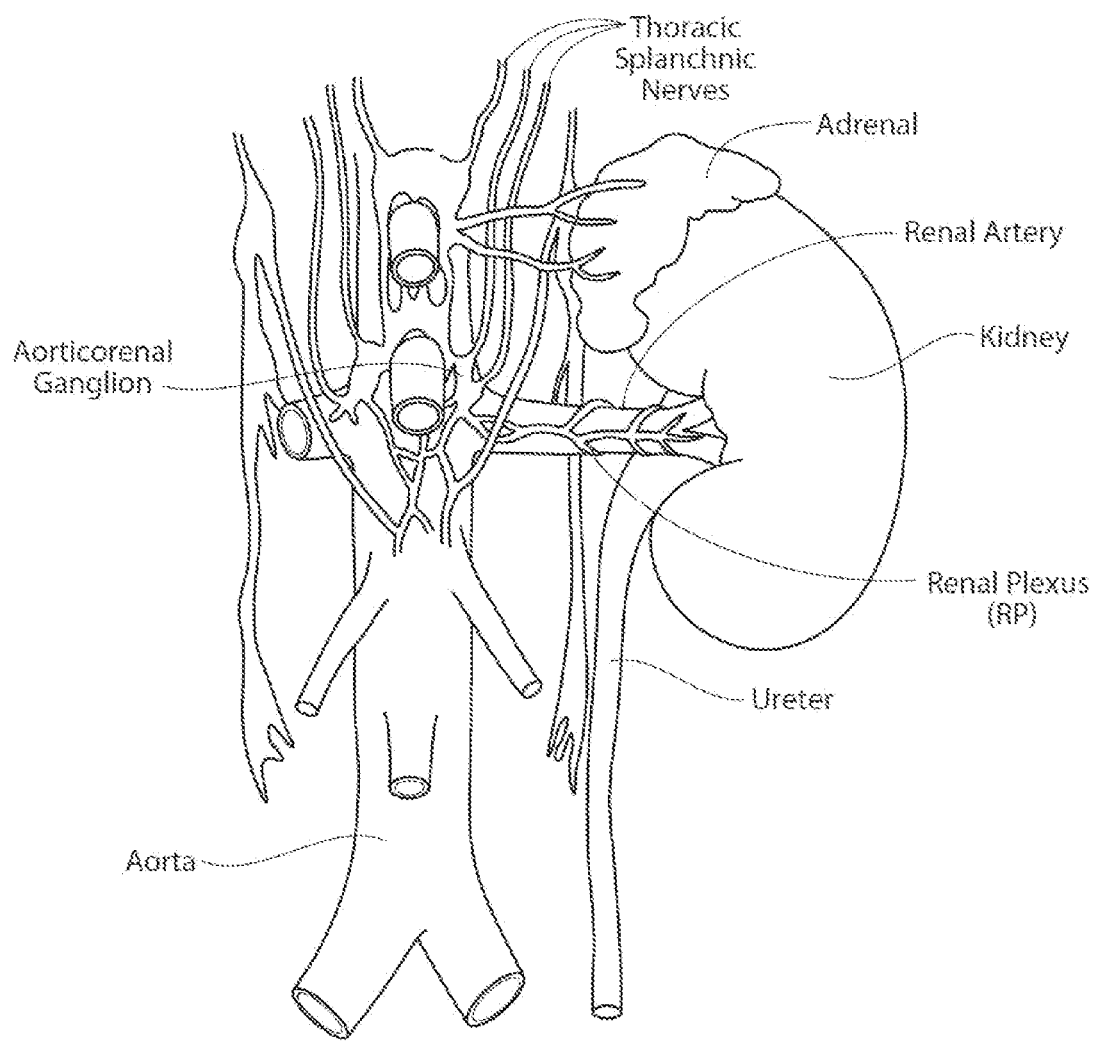
FIG. 12 is an enlarged anatomical view illustrating nerves innervating a left kidney to form a renal plexus surrounding a left renal artery.

As shown in FIG. 12, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. Accordingly, the renal plexus (RP) includes renal nerves and therefore modulating the renal plexus is one way to modulate a renal nerve. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aortico-renal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 13A:
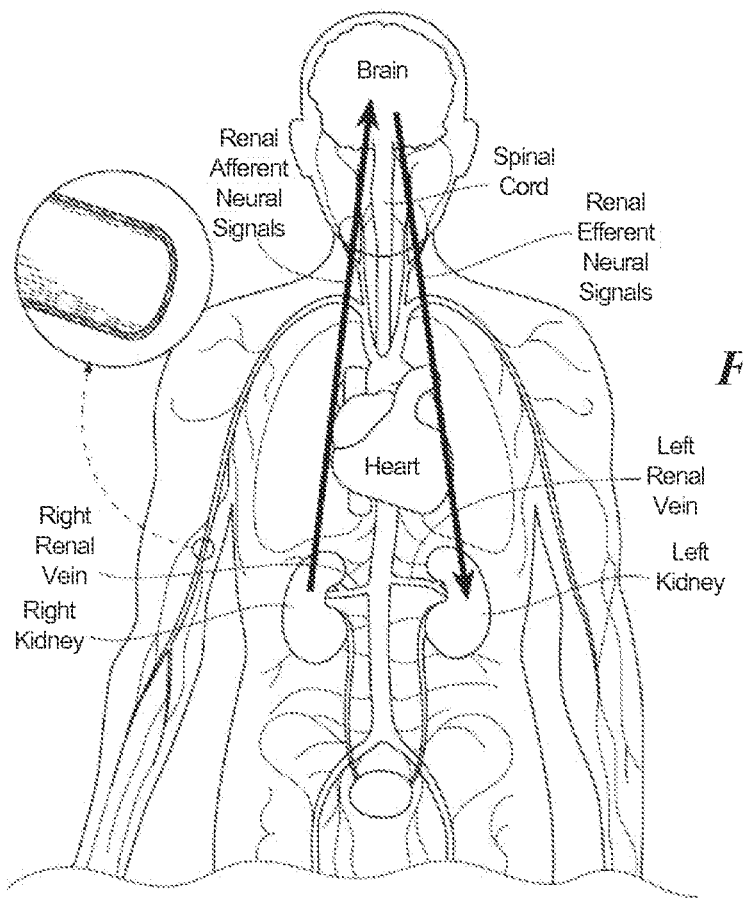
FIGS. 13A and 13B are anatomical and conceptual views, respectively, illustrating a human body including a brain and kidneys and neural efferent and afferent communication between the brain and kidneys.
Figure 13B:
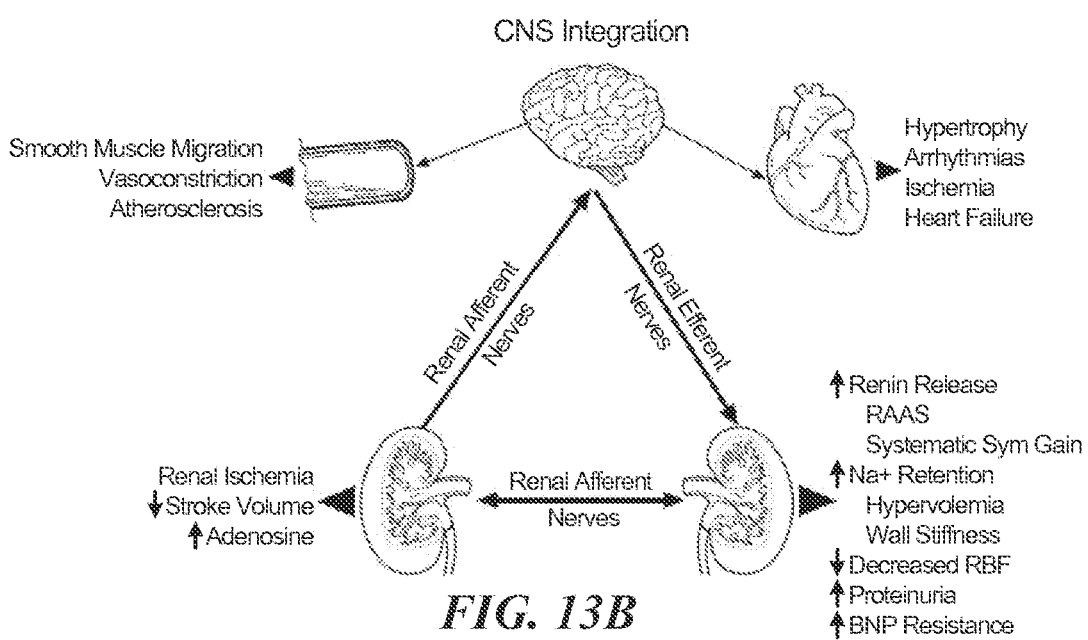

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 13A and 13B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 11. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 14A:
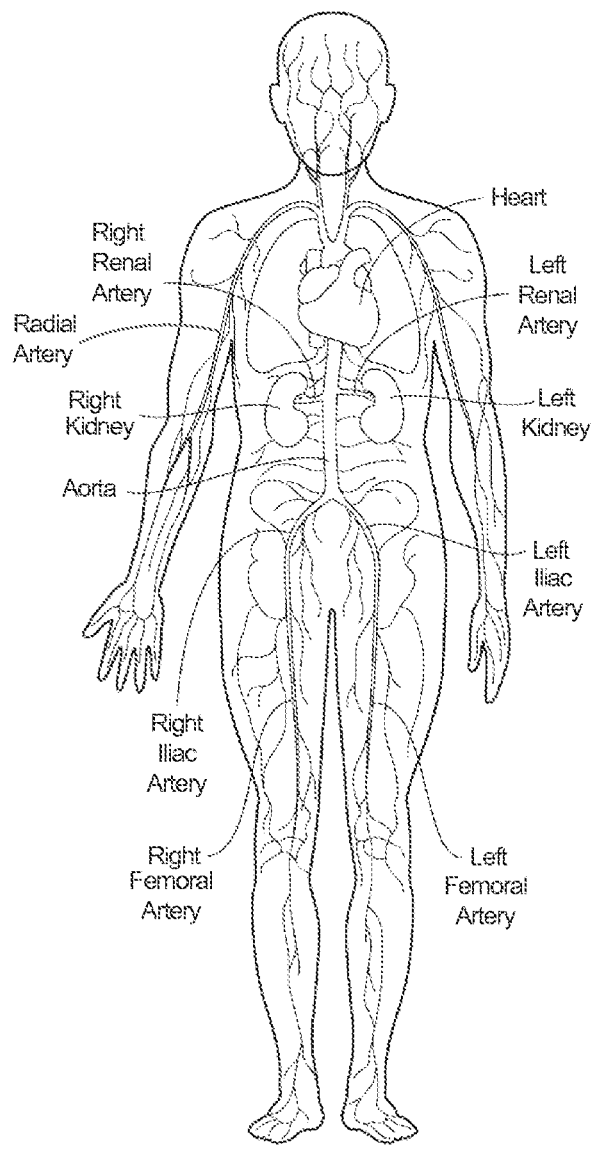
FIGS. 14A and 14B are anatomic views illustrating, respectively, an arterial vasculature and a venous vasculature of a human.

In accordance with the present technology, neuromodulation of a left and/or right renal plexus (RP), which is intimately associated with a left and/or right renal artery, may be achieved through intravascular access. As FIG. 14A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 14B:
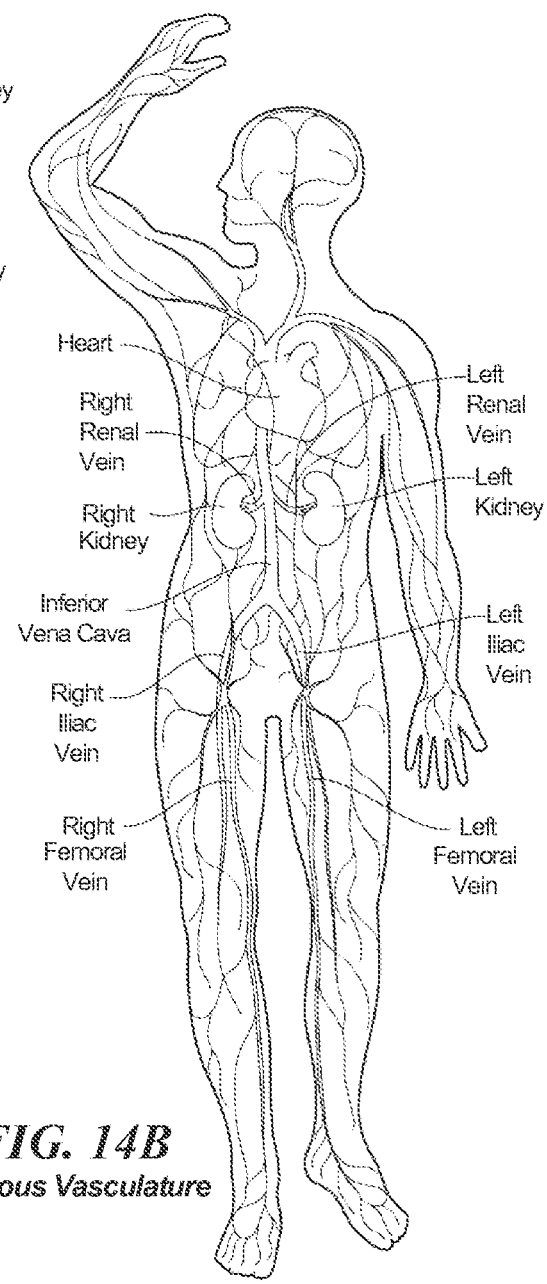

As FIG. 14B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesions likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IX. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method, comprising:
   emitting diagnostic energy from an emitter of a treatment assembly transluminally positioned within a body lumen of a human, wherein the diagnostic energy is emitted toward target tissue at least proximate to the wall of the body lumen;
   detecting a raw reflected signal of return energy associated with the emitted diagnostic energy and/or statistics based on the raw reflected signal;
   comparing the raw reflected signal and/or the statistics based on the raw reflected signal to at least one predetermined value;
   characterizing the target tissue based on the comparison;
   based, at least in part on (i) the raw reflected signal and/or on the statistics based on the raw reflected signal and/or (ii) the comparison to the at least one predetermined value, determining—
     a proximity of a neuromodulation element of the treatment assembly to the wall of the body lumen, and
     a circumferential proximity of the neuromodulation element to neural tissue; comparing—
     the proximity of the neuromodulation element to the wall of the body lumen to a predetermined proximity range, wherein the predetermined proximity range corresponds to sufficient contact between the neuromodulation element and the wall of the body lumen, and
     the circumferential proximity to a predetermined circumferential proximity range;
   using the comparison to the predetermined proximity range to indicate whether the neuromodulation element of the treatment assembly is within the predetermined proximity range; and
   using the comparison to the predetermined circumferential proximity range to indicate whether the tissue characterization identifies the neural tissue within the predetermined circumferential proximity range.

2. The method of claim 1, further comprising modulating nerves associated with renal function by delivering energy via the neuromodulation element of the treatment assembly positioned within the body lumen, wherein modulating the nerves associated with renal function includes initiating modulation and/or selecting a modulation parameter based on the tissue characterization.

3. The method of claim 2 wherein modulating the renal nerves includes delivering radio frequency ("RF") energy to the renal nerves.

4. The method of claim 1 wherein emitting diagnostic energy includes emitting diagnostic ultrasound energy.

5. The method of claim 1, further comprising transluminally positioning the treatment assembly within the body lumen of the human.

6. The method of claim 5, wherein transluminally positioning the treatment assembly comprises inserting the treatment assembly into one of the renal artery or the ureter.

7. The method of claim 1, further comprising:
   based, at least in part, or (i) the raw reflected signal and/or on the statistics based on the raw reflected signal and/or (ii) the comparison to the at least one predetermined value, determining a radial proximity of the neuromodulation element to the neural tissue;
   comparing the radial proximity to a predetermined radial proximity range; and
   using the comparison to the predetermined radial proximity range to indicate whether the tissue characterization identifies the neural tissue within the predetermined radial proximity range.

8. A method, comprising:
   emitting a first diagnostic energy emission from an emitter of a treatment assembly intravascularly positioned within a renal blood vessel of a human patient, wherein the diagnostic energy is emitted toward target tissue at least proximate to the wall of the renal blood vessel;
   detecting a first raw reflected signal of return energy associated with the first diagnostic energy emission and/or statistics based on the first raw reflected signal, the first raw reflected signal of return energy and/or the statistics based on the first raw reflected signal including at least one of a first detection time of the return energy, a first amplitude, and a first frequency;
   comparing the first raw reflected signal and/or the statistics based on the first raw reflected signal to at least one predetermined value;
   using the comparison to determine when a neuromodulation element of the treatment assembly is within a predetermined proximity range of the wall of the renal blood vessel, wherein the predetermined proximity range corresponds to sufficient contact between the neuromodulation element and the wall of the renal blood vessel;
   using the comparison to determine a relative position of at least a portion of the treatment assembly, the relative position including a circumferential proximity between at least a portion of the treatment assembly and target renal nerves within the tissue and a radial proximity between at least a portion of the treatment assembly and the target renal nerves;
   after determining the relative position, emitting a second diagnostic energy emission from the treatment assembly toward the target tissue while the renal nerves are modulated by delivering energy via the neuromodulation element of the treatment assembly;
   detecting a second raw reflected signal of return energy associated with the second diagnostic energy emission and/or statistics based on the second raw reflected signal, the second raw reflected signal of return energy and/or the statistics based on the second raw reflected signal including at least one of a second detection time of the returned energy, a second amplitude, and a second frequency;

comparing the second raw reflected signal and/or the statistics based on the second raw reflected signal to a second predetermined value; and determining a tissue characteristic based on a difference between (i) the first raw reflected signal of returned energy and/or the statistics based on the first raw reflected signal and (ii) the second raw reflected signal of returned energy and/or the statistics based on the second raw reflected signal.

9. The method of claim 8 wherein the tissue characteristic includes a depth of a lesion.

10. The method of claim 8 wherein the tissue characteristic includes a temperature of the tissue.

11. The method of claim 8 wherein the tissue characteristic includes a degree of tissue damage.

12. The method of claim 8 wherein emitting a first diagnostic energy emission and/or emitting a second diagnostic energy emission includes emitting ultrasound energy.

13. The method of claim 8 wherein emitting a first diagnostic energy emission and/or emitting a second diagnostic energy emission includes emitting electromagnetic energy.

14. The method of claim 8, further comprising intravascularly positioning the emitter of the treatment assembly within the renal blood vessel of the human patient.

15. A method for treating a human patient via an intravascularly delivered treatment assembly within a blood vessel of the patient, wherein nerves associated with renal function are located in tissue at least proximate a wall of the blood vessel, the method comprising:

emitting diagnostic energy from an emitter of the treatment assembly within the blood vessel toward tissue at least proximate to the wall of the blood vessel;

detecting a raw reflected signal of return energy associated with the emitted diagnostic energy and/or statistics based on the raw reflected signal;

comparing the raw reflected signal and/or the statistics based on the raw reflected signal to at least one predetermined value;

characterizing the target tissue based on the comparison based, at least in part, on (i) the raw reflected signal and/or on the statistics based on the raw reflected signal and/or (ii) the comparison to the at least one predetermined value, determining— a proximity of an energy delivery element of the treatment assembly to the wall of the blood vessel, and a circumferential proximity of the energy deliver element to neural tissue; comparing— the proximity of the energy delivery element to the wall of the blood vessel to a predetermine proximity range, wherein the predetermined proximity range correspond to sufficient contact between the neuromodulation element and the wall of the body lumen, and range;

determining, based on the comparison to the predetermined proximity range, whether the energy delivery element is within the predetermined proximity range;

determining, based on the comparison to the predetermined circumferential proximity range, whether the energy delivery element is within the predetermined circumferential proximity range; and in response to determining that the energy deliver element is within the predetermined proximity range of the wall of the blood vessel and is within the predetermined circumferential proximity range of the neural tissue, instructing an operator to begin modulating the nerves associated with renal function via energy delivery from the energy delivery element positioned within the blood vessel.

16. The method of claim 15 wherein emitting diagnostic energy from an emitter of the treatment assembly comprises emitting diagnostic ultrasound energy.

17. The method of claim 15, further comprising modulating the nerves associated with renal unction via the energy delivery from the energy delivery element, wherein modulating the nerves comprises delivering radio frequency (RF) energy via the energy delivery element.

18. The method of claim 15, further comprising modulating the nerves associated with renal function via the energy delivery from the energy delivery element, wherein modulating the nerves comprises at least partially ablating the nerves via the energy delivery from the energy delivery element.

19. The method of claim 15, further comprising modulating the nerves associated with renal function via the energy delivery from the energy delivery element, wherein the energy delivery element is an expandable neuromodulation element, and wherein modulating the nerves comprises delivering radio frequency (RF) energy from an array of electrodes carried by the expandable neuromodulation element.

20. The method of claim 15, further comprising:

based, at least in part, on (i) the raw reflected signal and/or on the statistics based on the raw reflected signal and/or (ii) the comparison to the at least one predetermined value, determining a radial proximity of the energy delivery element to the neural tissue;

comparing the radial proximity to a predetermined radial proximity range; and determining, based on the comparison to the predetermined radial proximity range, whether the energy delivery element is within the predetermined radial proximity range, wherein instructing the operator to begin modulating the nerves associated with renal function is further in response to determining that the energy delivery element is within the predetermined radial proximity range.

* * * * *